United States Patent
Tatsuta et al.

(10) Patent No.: US 12,059,126 B2
(45) Date of Patent: Aug. 13, 2024

(54) ENDOSCOPE SYSTEM

(71) Applicant: FUJIFILM Corporation, Tokyo (JP)

(72) Inventors: Takeichi Tatsuta, Kanagawa (JP);
Shinichiro Sonoda, Kanagawa (JP);
Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 898 days.

(21) Appl. No.: 16/297,736

(22) Filed: Mar. 11, 2019

(65) Prior Publication Data
US 2019/0204069 A1 Jul. 4, 2019

Related U.S. Application Data

(63) Continuation of application No. PCT/JP2017/028645, filed on Aug. 7, 2017.

(30) Foreign Application Priority Data

Sep. 15, 2016 (JP) ................ 2016-180809

(51) Int. Cl.
*A61B 1/00* (2006.01)
*A61B 1/045* (2006.01)
(Continued)

(52) U.S. Cl.
CPC ...... *A61B 1/00045* (2013.01); *A61B 1/00009* (2013.01); *A61B 1/00096* (2013.01);
(Continued)

(58) Field of Classification Search
CPC ............ A61B 1/00009; A61B 1/00045; A61B 1/00165; A61B 1/00179; A61B 1/045;
(Continued)

(56) References Cited

U.S. PATENT DOCUMENTS

2009/0093681 A1* 4/2009 Ichimura ............ A61B 1/0623
600/178
2011/0074950 A1 3/2011 Oka et al.
(Continued)

FOREIGN PATENT DOCUMENTS

CN 104146711 11/2014
CN 104146711 A * 11/2014 ........... G01B 11/026
(Continued)

OTHER PUBLICATIONS

"Search Report of Europe Counterpart Application", issued on Sep. 18, 2019, p. 1-p. 10.
(Continued)

*Primary Examiner* — Aaron B Fairchild
*Assistant Examiner* — Stephen Floyd London
(74) *Attorney, Agent, or Firm* — JCIPRNET

(57) ABSTRACT

An endoscope system capable of easily measuring a size of a subject is provided. In the endoscope system, since an index figure indicating an actual size of a specific region of a test object is displayed together with an image of the subject, a user can measure the specific region easily by comparing the specific region with a marker. Since the size of the index figure is set in accordance with a spot position, there is no need for distance measurement, a device configuration is simple, and measurement can be quickly and easily performed. In addition, a specific value of the "actual size" can be set in accordance with conditions, such as the type of test object and the purposes of measurement. Additionally, an affected region can be the specific region in a case where the test object is a living body.

13 Claims, 27 Drawing Sheets

(51) Int. Cl.
*A61B 1/06* (2006.01)
*A61B 5/06* (2006.01)
*A61B 5/107* (2006.01)
*G01B 11/02* (2006.01)
*G01B 11/14* (2006.01)
*G01B 11/25* (2006.01)
*G01B 21/04* (2006.01)
*G01N 21/954* (2006.01)
*G02B 23/24* (2006.01)
*G06T 7/00* (2017.01)

(52) U.S. Cl.
CPC .......... *A61B 1/00097* (2022.02); *A61B 1/045* (2013.01); *A61B 1/063* (2013.01); *A61B 1/0676* (2013.01); *A61B 5/064* (2013.01); *A61B 5/1076* (2013.01); *G01B 11/02* (2013.01); *G01B 11/026* (2013.01); *G01B 11/028* (2013.01); *G01B 11/14* (2013.01); *G01B 11/25* (2013.01); *G01B 21/045* (2013.01); *G01N 21/954* (2013.01); *G02B 23/24* (2013.01); *G02B 23/243* (2013.01); *G02B 23/2461* (2013.01); *G06T 7/0012* (2013.01)

(58) Field of Classification Search
CPC . A61B 1/0623; A61B 1/0638; A61B 1/00096; A61B 1/0125; A61B 1/018; A61B 5/1076; A61B 5/1079; H04N 2005/2255; G02B 23/2461; G02B 23/2469
See application file for complete search history.

(56) References Cited

U.S. PATENT DOCUMENTS

| | | | | |
|---|---|---|---|---|
| 2011/0082369 | A1* | 4/2011 | Mohr | A61B 1/00009 |
| | | | | 600/431 |
| 2011/0187824 | A1* | 8/2011 | Hori | H04N 13/00 |
| | | | | 348/E13.001 |
| 2013/0144186 | A1* | 6/2013 | Furlong | A61B 10/04 |
| | | | | 600/568 |
| 2014/0036050 | A1* | 2/2014 | Yoshino | H04N 5/23229 |
| | | | | 348/65 |
| 2016/0287141 | A1* | 10/2016 | Sidlesky | G02B 23/2415 |

FOREIGN PATENT DOCUMENTS

| | | | |
|---|---|---|---|
| EP | 2698983 | | 2/2014 |
| JP | 59-069046 | A * | 4/1984 |
| JP | S5969046 | | 4/1984 |
| JP | S6273223 | | 4/1987 |
| JP | H07136101 | | 5/1995 |
| JP | H07136101 | A * | 5/1995 |
| JP | H08285541 | | 11/1996 |
| JP | 3446272 | | 9/2003 |
| JP | 2008122759 | | 5/2008 |
| JP | 2011069965 | | 4/2011 |
| JP | 2011139734 | | 7/2011 |
| WO | 2012141088 | | 10/2012 |
| WO | WO-2017199657 | A1 * | 11/2017 ............... A61B 1/00 |

OTHER PUBLICATIONS

Office Action of Japan Counterpart Application, with English translation thereof, issued on Apr. 6, 2021, pp. 1-8.
"International Search Report (Form PCT/ISA/210) of PCT/JP2017/028645," mailed on Oct. 17, 2017, with English translation thereof, pp. 1-5.
"Written Opinion of the International Searching Authority (Form PCT/ISA/237) of PCT/JP2017/028645," mailed on Oct. 17, 2017, with English translation thereof, pp. 1-9.
"Office Action of Japan Counterpart Application," with English translation thereof, issued on Jan. 29, 2020, p. 1-p. 6.

* cited by examiner

FIG. 16

| | | |
|---|---|---|
| NUMBER OF MARKERS (C01) | 1 (V01) | ▼ (A01) |
| SHAPE (C02) | CROSS (V02) | ▼ (A02) |
| SIZE (C03) | 5mm (V03) | ▼ (A03) |
| COLOR (C04) | WHITE (V04) | ▼ (A04) |
| NUMERICAL VALUE DISPLAY (C05) | ON (V05) | ▼ (A05) |
| DISTORTION CORRECTION (C06) | OFF (V06) | ▼ (A06) |
| OFFSET DISPLAY (C07) | OFF (V07) | ▼ (A07) |
| GRADUATION DISPLAY (C08) | OFF (V08) | ▼ (A08) |

OK (B01)   CANCEL (B02)   CLEAR (B03)

FIG. 17

| C01 | V01 | | |
|---|---|---|---|
| NUMBER OF MARKERS | 1 | △ | A01a |
| | 2 | ≡ | A01c |
| | 3 | | A01 |
| | 4 | | |
| | 5 | ▽ | A01b |

B01 OK    B02 CANCEL    B03 CLEAR

FIG. 18

| C02 | V02 | | |
|---|---|---|---|
| MARKER 1: SHAPE | CROSS | △ | A02a |
| | GRADUATED CROSS | | |
| | POINT | ≡ | A02c — A02 |
| | CIRCLE | | |
| | CIRCLE + CROSS | ▽ | A02b |

B01 OK    B02 CANCEL    B03 CLEAR

FIG. 19

MARKER 1: SIZE — C03

V03: 2mm / 3mm / 5mm / 7mm / 10mm

A03a △
A03c ≡
A03b ▽
} A03

B01 OK   B02 CANCEL   B03 CLEAR

FIG. 20

MARKER 1: COLOR — C04

V04: RED / BLUE / WHITE / BLACK / YELLOW / GREEN

A04a △
A04c ≡
A04b ▽
} A04

B01 OK   B02 CANCEL   B03 CLEAR x (X-DIRECTION PIXEL POSITION OF SPOT)

y (Y-DIRECTION PIXEL POSITION OF SPOT)

x (X-DIRECTION PIXEL POSITION OF SPOT)

ENDOSCOPE SYSTEM

CROSS-REFERENCE TO RELATED APPLICATIONS

The present application is a Continuation of PCT International Application No. PCT/JP2017/028645 filed on Aug. 7, 2017 claiming priority under 35 U.S.C § 119(a) to Japanese Patent Application No. 2016-180809 filed on Sep. 15, 2016. Each of the above applications is hereby expressly incorporated by reference, in their entirety, into the present application.

BACKGROUND OF THE INVENTION

1. Field of the Invention

The present invention relates to an endoscope system, and particularly, to an endoscope system that measures the size of a test object using measurement auxiliary light.

2. Description of the Related Art

In the field of endoscopes, measuring the distance to a test object or calculating the length and the size of the test object is performed. For example, JP2008-122759 discloses that a subject distance is measured by a stereoscopic camera, and the size of a mark serving as a rough standard of the size of a subject is calculated on the basis of the subject distance and the visual field angle of an endoscope, and the mark is described together with an image of the subject, and the size of the subject can be known from this mark.

Additionally, JP1996-285541 (JP-H08-285541A) discloses a technique of finding a subject distance by using measurement auxiliary light. In JP1996-285541, an irradiation surface is observed by radiating a laser beam from the optical fiber. Then, by utilizing the fact a radiation point of the laser beam is brought close to or separated from the center of a visual field depending on the distance from the optical fiber to the irradiation surface and by correcting the amount of deviation in advance, the subject distance can be known from the amount of deviation.

SUMMARY OF THE INVENTION

However, in the above-described JP2008-122759, in order to measure the distance with the stereoscopic camera, two cameras are required, and a distal end part of the endoscope increases. Therefore, a burden to the test object is large. Moreover, since the distance measurement is performed and the size of the mark is calculated on the basis of the result, processing is complicated. Additionally, the technique disclosed in JP1996-285541 is for performing the distance measurement, and the processing is complicated, and it is difficult to find the length and the size of the subject.

In this way, in the related-art technique, the size (length) of the subject cannot be easily measured.

The invention has been made in view of such circumstances, and an object thereof is to provide an endoscope system capable of easily measuring the size of a subject.

In order to achieve the above-described object, an endoscope system related to a first aspect of the invention is an endoscope system including an endoscope that acquires an image of a test object. The endoscope system comprises an auxiliary light radiation unit that radiates measurement auxiliary light to the subject; an imaging unit that acquires the image of the subject, on which a spot is formed with the measurement auxiliary light, via an imaging optical system and an imaging element; a display device that displays the acquired image of the subject; and a processor that makes the display device display, together with the image of the subject, an index figure indicating an actual size of a specific region in the subject and having a size set in accordance with a position of the spot on the imaging element as the imaging unit acquires the image of the subject. According to the first aspect, since the index figure (marker) indicating the actual size of the specific region of a test object is displayed together with the image of the subject, a user can measure the specific region easily by comparing the specific region with the marker. In addition, a specific value of the "actual size" can be set in accordance with conditions, such as the type of test object or the purposes of measurement. Additionally, an affected region or the like can be the specific region (region of interest) in a case where the test object is a living body.

In the first aspect, since the size of the index figure is set in accordance with a spot position, unlike the above-described JP2008-122759 and JP1996-285541 there is no need for distance measurement, a device configuration is simple, and measurement can be quickly and easily performed. In addition, in the first aspect, it is preferable that the setting of the size of the index figure is performed in real time. However, in a case where a demand for a real-time property is not high in observation and measurement, the setting is not necessarily in real time.

In the first aspect, the size of the index figure can be set by storing "the information indicating the relationship between spot positions and actual sizes of subjects" in advance and referring to this information according to a measured spot position. Additionally, in the first aspect, laser light, LED light, or the like can be used as the measurement auxiliary light. The measurement auxiliary light may be the light made parallel by a collimator.

In the endoscope system related to a second aspect based on the first aspect, the processor makes the index figure distorted in accordance with a distortion aberration of the imaging optical system be displayed. In many cases, endoscopes generally have a wide observation field angle, and particularly, have large distortion correction at a peripheral portion of the field angle. In a second aspect, the influence of the distortion aberration of the imaging optical system is corrected in a case where the index figure is displayed on the display device (screen). Data of the distortion aberration may be set on the basis of design values of the imaging optical system or may be separately measured.

In the endoscope system related to a third aspect based on the first aspect, the processor makes the index figure displayed together with the image of the subject corrected in accordance with a distortion aberration of the imaging optical system. According to the third aspect, since the image of the subject is corrected in accordance with the distortion aberration of the imaging optical system, the shape or the like of the subject can be accurately displayed and can be measured with high accuracy.

In the endoscope system related to a third aspect based on any one of the first to fourth aspects, the processor makes the image of the subject and the index figure be displayed in a state where a center of the index figure coincide with a center of the spot. According to the fourth aspect, since the center of the index figure is made to coincide with the center of the spot, the spot position and the size of the index figure can be accurately made to respond to each other, and can be measured with high accuracy.

In the endoscope system related to a fifth aspect based on any one of the first to third aspects, the processor makes the image of the subject and the index figure be displayed in a state where a center of the index figure is separated from a center of the spot. In the fifth aspect, in a case where the observation target confronts (is inclined with respect to) the endoscope, this is effective.

In the endoscope system related to a sixth aspect based on any one of the first to fifth aspects, the processor makes the index figure of a size corresponding to a single value of the actual size be displayed. In the sixth aspect, the index figure of the size corresponding to the single value of the actual size, that is, one index figure, is displayed.

In the endoscope system related to a seventh aspect based on any one of the first to sixth aspects, the processor makes the index figure of a size corresponding to a value selected from a plurality of values of the actual sizes be displayed. According to the seventh aspect, an index figure of a desired size can be displayed in accordance with the type of a subject or observation purposes.

The endoscope system related to an eighth aspect based on the seventh aspect further comprises a selection unit that receives a user's selection operation for the plurality of values, and the processor makes one or a plurality of the index figures of the size corresponding to the value selected on the basis of the selection operation from the plurality of values displayed. According to the eighth aspect, the user can display the index figure of a desired number and a desired size in accordance with the type of subject or observation purposes.

In the endoscope system related to a ninth aspect based on any one of the first to fifth aspects, the processor makes the index figure of a size corresponding to a combination of a plurality of values of the actual sizes be displayed. According to the ninth aspect, the index figure can be displayed with a combination of desired sizes in accordance with the type of subject or observation purposes.

The endoscope system related to a tenth aspect based on the ninth aspect further comprises a selection unit that receives a user's selection operation for the combination of the plurality of values, the processor makes the index figure of a size corresponding to a combination selected on the basis of the selection operation displayed. According to the tenth aspect, the user can display the index figure of a desired combination in accordance with the type of subject or observation purposes.

In the endoscope system related to an eleventh aspect based on any one of the first to tenth aspects, the processor makes the index figure having a different color displayed in correspondence with a value of the actual size. According to the eleventh aspect, a different index figure can be quickly and easily viewed depending on a difference in color.

In the endoscope system related to a twelfth aspect based on any one of the first to eleventh aspects, the auxiliary light radiation unit radiates, as the measurement auxiliary light, measurement auxiliary light of which an optical axis forms an angle, which is not 0 degrees, with an optical axis of the imaging optical system, and, in a case where a distance between the imaging unit, as well as the auxiliary light radiation unit, and the subject is changed in a direction of the optical axis of the imaging optical system, a position of the spot on the imaging element in a case where the distance is a longest range of a length measurement distance range of the endoscope is opposite to a position of the spot on the imaging element in a case where the distance is an closest range of the length measurement distance range, with a position of the optical axis of the imaging optical system in the imaging element interposed therebetween.

In a case where the angle at which the optical axis of the measurement auxiliary light is formed with the optical axis of the imaging optical system is 0 degrees (the optical axis of the imaging optical system is parallel to the optical axis of the measurement auxiliary light) like the above-described JP1996-285541, the position of the spot on the imaging element only approaches the center of the imaging element (the position of the optical axis of the imaging element) as the observation distance becomes farther, the positions of the spot on the imaging element are not opposite to each other with the position of the optical axis of the imaging optical system interposed therebetween in cases of the longest range and the closest range. In contrast, according to the twelfth aspect, the optical axis of the measurement auxiliary light forms the angle, which is not 0 degrees, with the optical axis of the imaging optical system. Thus, by appropriately setting the inclination angle, the measurement auxiliary light can enter the visual field of the imaging optical system even in a case where the observation distance is short. Additionally, since the sensitivity of a change in the position of the spot with respect to a change in the observation distance becomes high, measurement can be made with high accuracy. In addition, the angle at which the optical axis of the measurement auxiliary light is formed with the optical axis of the imaging optical system can be defined in a state where the optical axis of the measurement auxiliary light is projected on a plane including the optical axis of the imaging optical system.

In addition, in the twelfth aspect, the "length measurement distance range" means a range of an observation distance that can be measured. Additionally, in the twelfth aspect, it is preferable that the measurement auxiliary light is the light made parallel by the collimator.

As described above, according to the endoscope system of the invention, the size of the subject can be easily and highly accurately measured.

BRIEF DESCRIPTION OF THE DRAWINGS

FIG. 16 is a view illustrating an example of a marker display condition setting screen.

FIG. 17 is a view illustrating an example of a number-of-markers display condition setting screen.

FIG. 18 is a view illustrating an example of a screen where the shape of a marker is set.

FIG. 19 is a view illustrating an example of a screen where the size of a marker is set.

FIG. 20 is a view illustrating an example of a screen where the color of a marker is set.

DESCRIPTION OF THE PREFERRED EMBODIMENTS

Hereinafter, embodiments of an endoscope system related to the invention will be described in detail, referring to the accompanying drawings.

First Embodiment

Figure 1:
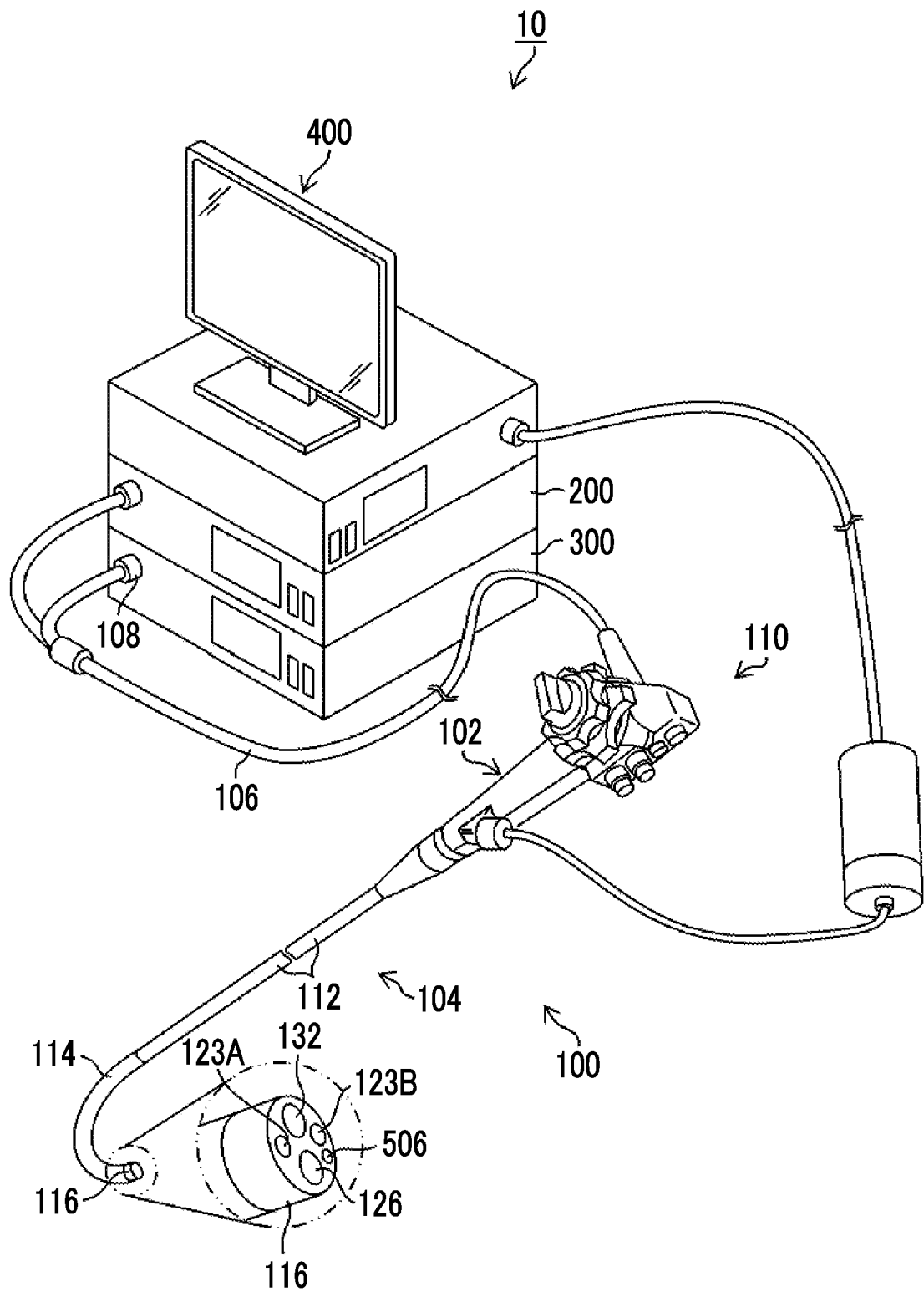
FIG. 1 is a view illustrating an overall configuration of an endoscope system related to a first embodiment of the invention.
Figure 2:
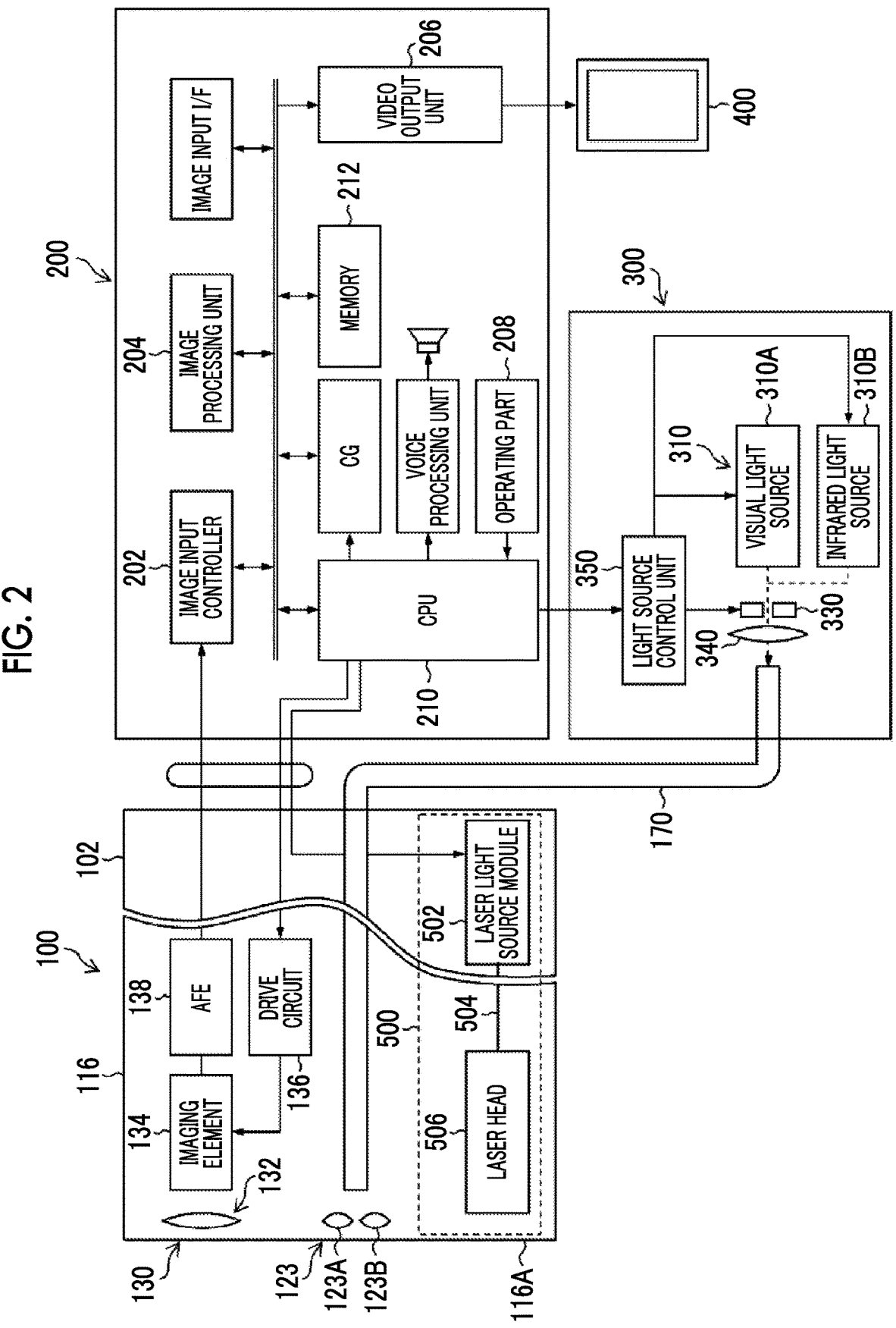
FIG. 2 is a block diagram illustrating the configuration of the endoscope system related to the first embodiment of the invention.

FIG. 1 is an external view illustrating an endoscope system 10 (endoscope system) related to a first embodiment, and FIG. 2 is a block diagram illustrating the configuration of main parts of the endoscope system 10. As illustrated in FIGS. 1 and 2, the endoscope system 10 includes an endoscope device 100 constituted of an endoscope body 110 (endoscope), an endoscope processor 200 (processor), a light source device 300, and a monitor 400 (a display device or a selection unit).

<Configuration of Endoscope Body>

The endoscope body 110 includes a proximal operating part 102, and an insertion part 104 consecutively installed at the proximal operating part 102. An operator grips and operates the proximal operating part 102, and performs observation by inserting the insertion part 104 into the body of a test object. The insertion part 104 is constituted of a flexible part 112, a bending part 114, and a distal end rigid part 116 sequentially from the proximal operating part 102 side. The distal end rigid part 116 is provided with an imaging optical system 130 (an imaging optical system or an imaging unit), an illumination unit 123, a forceps port 126, and a laser module 500 (auxiliary light radiation unit), and the like (refer to FIGS. 1 to 3).

During observation or treatment, visible light, infrared light, or both can be radiated from illuminating lenses 123A and 123B of the illumination unit 123 by the operation of an operating part 208 (refer to FIG. 2). Additionally, washing water is released from a water supply nozzle (not illustrated) by the operation of the operating part 208, so that an imaging lens 132 of the imaging optical system 130 and the illuminating lenses 123A and 123B can be washed. A pipe line (not illustrated) communicates with the forceps port 126 that opens at the distal end rigid part 116, and a treatment tool (not illustrated) for tumor removal or the like is inserted through to the pipe line is appropriately moved forward and backward so as to perform treatment required for the test object.

Figure 3:
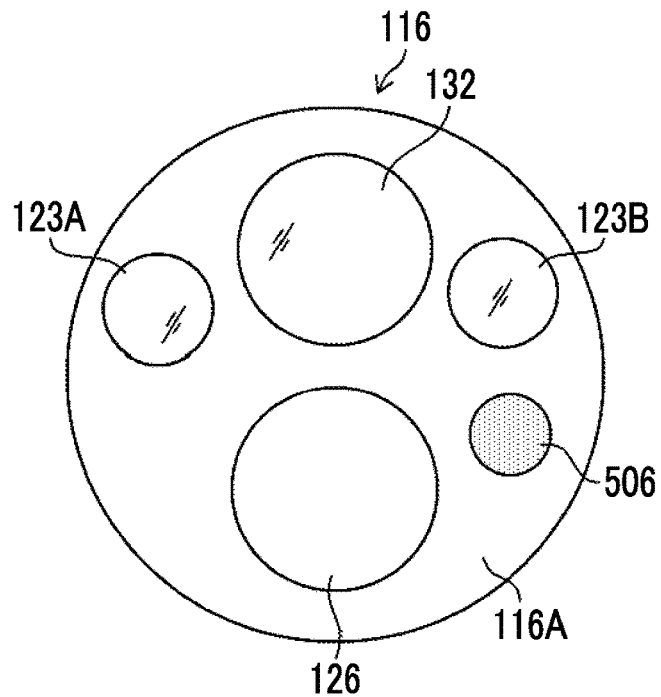
FIG. 3 is a view illustrating the configuration of a distal-end-side end surface of a distal end rigid part.

As illustrated in FIGS. 1 to 3, the imaging lens 132 is disposed on a distal-end-side end surface 116A of the distal end rigid part 116, and a complementary metal oxide semiconductor (CMOS) type imaging element 134 (an imaging element or an imaging unit), a drive circuit 136, and an analog front end (AFE) 138 are disposed at the back of the imaging lens 132 so as to output image signals. The imaging element 134 is a color imaging element, and includes a plurality of pixels constituted of a plurality of light receiving elements arranged in a matrix (two-dimensionally) in a specific pattern array (a Bayer array, a G-stripe RIB perfect checker, an X-Trans (registered trademark) array, a honeycomb array, or the like). Each pixel includes a microlens, a red (R), green (G), or blue (B) color filter, and a photoelectric conversion part (photodiode or the like). The imaging optical system 130 may create a color image from pixel signals of three colors of red, green, and blue, or may create an image from pixel signals of any one color or two colors among red, green, and blue.

In addition, in the first embodiment, a case where the imaging element 134 is a CMOS type imaging element is described. However, the imaging element 134 may be of charge coupled device (CCD) type.

An image of the test object (a specific region, such as an affected region) or an optical image of a spot (to be described below) is formed on a light-receiving surface (imaging surface) of the imaging element 134 by the imaging lens 132, is converted into electrical signals, is output to the endoscope processor 200 via a signal cable (not illustrated), and is converted into video signals. Accordingly, observation images, captured image of spots, images of markers (refer to FIGS. 23 to 29), and the like are displayed on the monitor 400 connected to the endoscope processor 200. In addition, the monitor 400 (the display device or the selection unit) includes a touch panel (the selection unit; not illustrated) that receives user's operations, and the user can perform operations (to be described below), such as observation mode switching and marker display condition setting, via this touch panel.

Additionally, the illuminating lenses 123A (for visible light) and 123B (for infrared light) of the illumination unit 123 are provided adjacent to the imaging lens 132 on the distal-end-side end surface 116A of the distal end rigid part 116. An exit end of a light guide 170 to be described below is disposed at the back of the illuminating lenses 123A and 123B, the light guide 170 is inserted through the insertion part 104, the proximal operating part 102, and a universal cable 106, and an incident end of the light guide 170 is disposed within a light guide connector 108.

Figure 4:
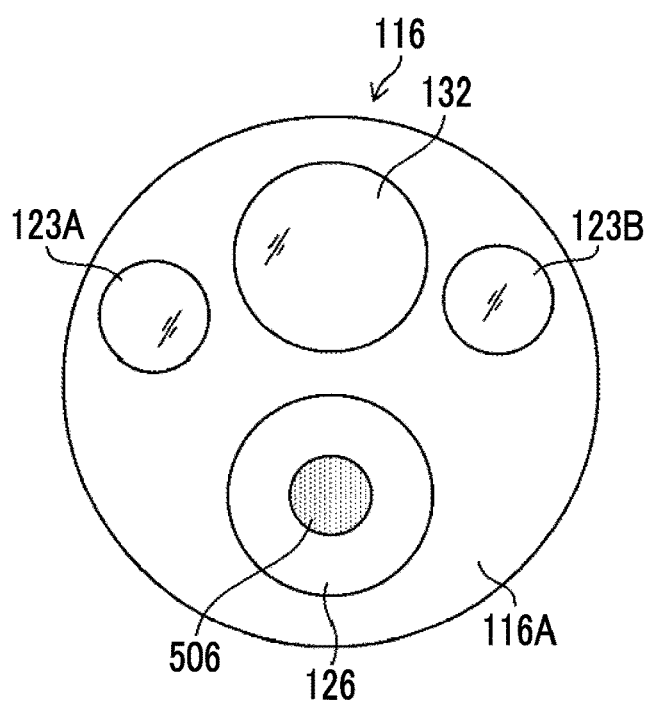
FIG. 4 is another view illustrating the configuration of the distal-end-side end surface of the distal end rigid part.

The distal-end-side end surface 116A is further provided with a laser head 506 of the laser module 500 and is irradiated with spot light (measurement auxiliary light) via a prism 512. The configuration of the laser module 500 will be described below. In addition, in the first embodiment, as illustrated in FIG. 3, the laser head 506 is provided separately from the forceps port 126. In the endoscope system related to the invention, as illustrated in FIG. 4, the laser head 506 may be removably inserted through the pipe line (not illustrated) that communicates with the forceps port 126 opening at the distal end rigid part 116. In this case, it is not necessary to provide a pipe line dedicated to the laser head 506, and the pipe line with that communicates with the forceps port 126 can be shared with other treatment tools.

<Configuration of Laser Module>

Figure 5:
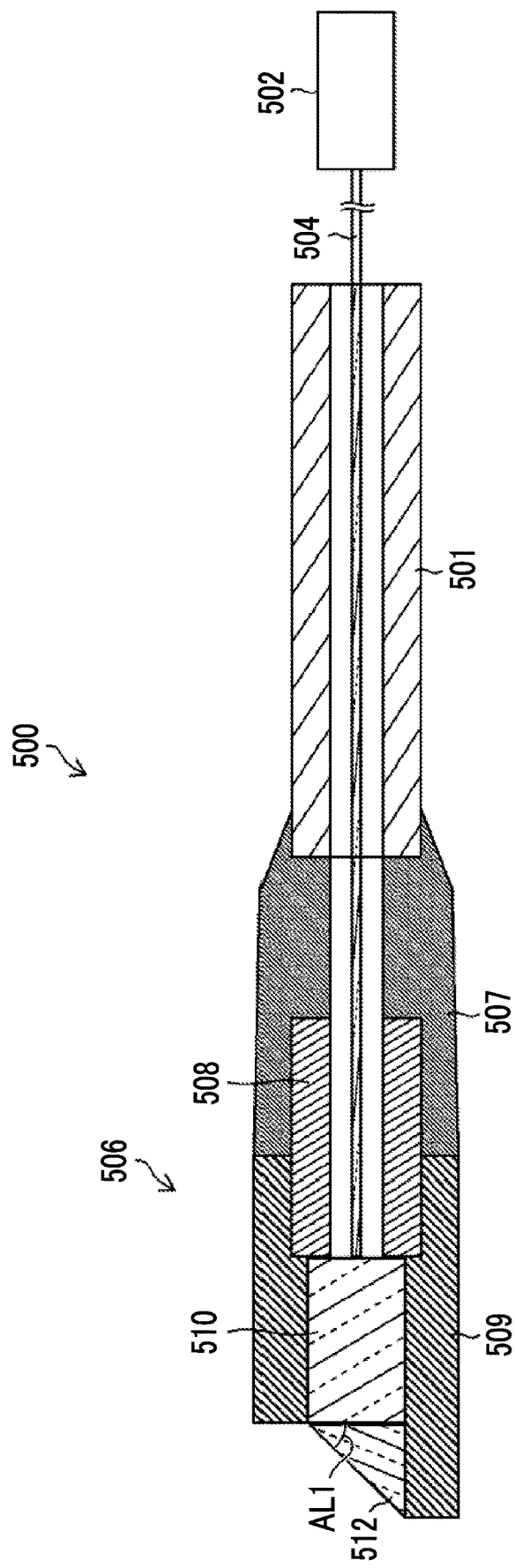
FIG. 5 is a view illustrating the configuration of a laser module.

As illustrated in FIGS. 2 and 5, the laser module 500 includes a laser light source module 502 (auxiliary light radiation unit), an optical fiber 504, and the laser head 506. A proximal end side (laser light source module 502 side) of the optical fiber 504 is covered with a fiber outer jacket 501, a distal end side (a side from which laser light is emitted) thereof is inserted into a ferrule 508 and is bonded with an adhesive, and an end surface is ground. A graded index (GRIN) lens 510 is mounted on a distal end side of the ferrule 508, and a prism 512 is mounted on a distal end side of the GRIN lens 510 so as to form a joined body. The ferrule 508 is a member for holding and connecting the optical fiber 504, and a hole for allowing the optical fiber 504 to be inserted therethrough is made empty in an axial direction (leftward-rightward direction of FIG. 5) at a central portion of the ferrule. A reinforcing member 507 is provided outside the ferrule 508 and the fiber outer jacket 501 to protect an optical fiber 504 or the like. The ferrule 508, the GRIN lens 510, and the prism 512 are housed in a housing 509 and are integrated with the reinforcing member 507 and the fiber outer jacket 501 to constitute the laser head 506.

In the laser head 506, for example, one having a diameter of 0.8 mm to 1.25 mm can be used as the ferrule 508. In addition, a fine-diameter ferrule is more preferable for downsizing. By virtue of the above-described configuration, the total diameter of the laser head 506 can be 1.0 mm to 1.5 mm.

The laser module 500 configured in this way is mounted on the insertion part 104. Specifically, as illustrated in FIG. 2, the laser light source module 502 is disposed at the portion of the proximal operating part 102 (scope) and is mounted on an electric circuit substrate part. Meanwhile, the laser head 506 is provided at the distal end rigid part 116, and the optical fiber 504 guides the laser light from the laser light source module 502 to the laser head 506. In addition, the laser light source module 502 may be provided within the light source device 300 so as to guide the laser light to the distal end rigid part 116 with the optical fiber 504.

Figure 6:
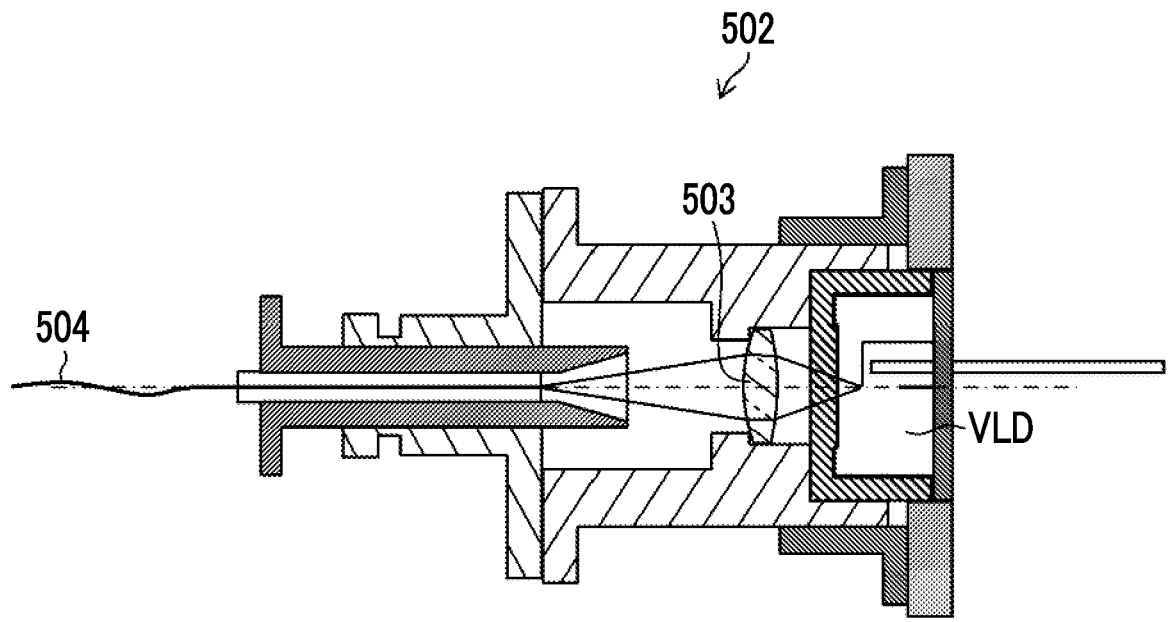
FIG. 6 is a sectional view illustrating the configuration of a laser light source module.

The laser light source module 502 is a pigtail type module (transmitter optical sub-assembly (TOSA)) including a visible laser diode (VLD) that has electrical power supplied thereto from a power source (not illustrated) and emits the laser light of a visible wavelength range, and a condensing lens 503 that condenses the laser light emitted from the VLD (refer to FIG. 6). The laser light can be emitted as necessary by the control of the endoscope processor 200 (CPU 210). By emitting the laser light only in a case where measurement is performed by radiation of spot light (measurement mode), the laser light can be used similarly to an ordinary endoscope during non-emission (normal mode). Turn-on, turn-off, and the intensity of light of the laser light source module 502 are controlled in accordance with the electrical signals from the endoscope processor 200.

In the first embodiment, the laser light emitted by the VLD can be red laser light with a wavelength of 650 nm by a semiconductor laser. However, the wavelength of the laser light in the invention is not limited to this aspect. The laser light condensed by the condensing lens 503 is guided up to the GRIN lens 510 by the optical fiber 504. The optical fiber 504 is an optical fiber that propagates the laser light in a single transverse mode, and can form a spot with a small clear diameter, so that the size of a subject can be accurately measured. A relay connector may be provided in the middle of the optical fiber 504. In addition, in a case where the size of spot diameter or clearness does not pose a measurement problem depending on observation conditions, such as the type or size of a subject, an optical fiber that propagates the laser light in a multi-mode may be used as the optical fiber 504. Additionally as the light source, a light-emitting diode (LED) may be used instead of the semiconductor laser, or the semiconductor laser may be used in an LED light emission state below an oscillation threshold value.

The GRIN lens 510 is a cylindrical graded index type lens (radial type) of which the refractive index is at the highest thereof on the optical axis and decrease radially outward, and functions as a collimator that makes the laser light, which is guided by the optical fiber 504 and entered, into a parallel beam and emits the parallel light. The spread of the beam emitted from the GRIN lens 510 can be adjusted by adjusting the length of the GRIN lens 510, and ($\lambda/4$) pitch ($\lambda$ is the wavelength of the laser light) or the like may be used to emit the laser light as the parallel beam.

The prism 512 is mounted on a distal end side of the GRIN lens 510. The prism 512 is an optical member for changing the emission direction of the measurement auxiliary light. By changing the emission direction, in a case where the optical axis of the measurement auxiliary light is projected on a plane including the optical axis of the imaging optical system, the optical axis of the measurement auxiliary light has an inclination angle (angle), which is not 0 degrees with respect to the optical axis of the imaging optical system, and the measurement auxiliary light crosses the field angle of the imaging optical system. The prism 512 is formed with a size near the lens diameter of the GRIN lens 510, and a distal end surface thereof is cut obliquely and has an apex angle AL1 according to the above-described inclination angle.

<Relationship Between Optical Axis of Imaging Optical System and Optical Axis of Measurement Auxiliary Light>

Figure 7:
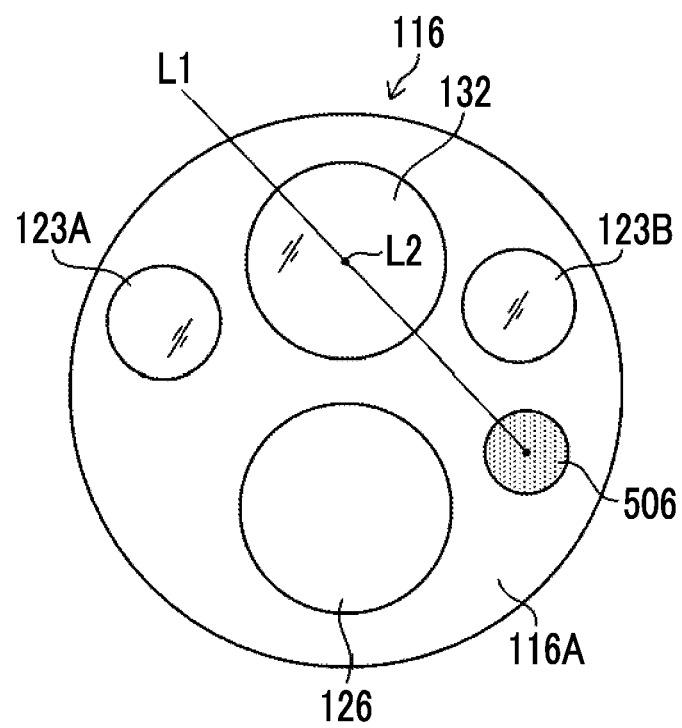
FIG. 7 is a view illustrating a relationship between an optical axis of an imaging optical system and an optical axis of measurement auxiliary light.
Figure 8:
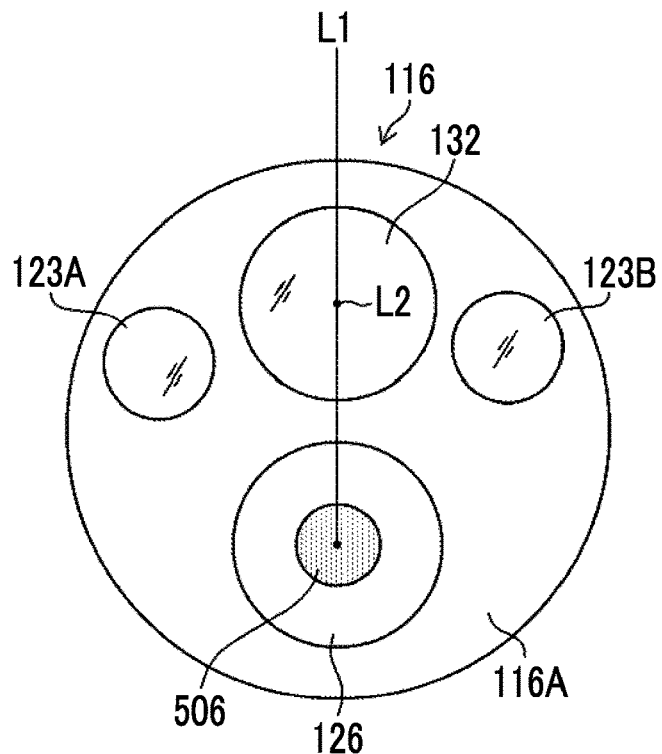
FIG. 8 is another view illustrating the relationship between the optical axis of the imaging optical system and the optical axis of the measurement auxiliary light.

FIG. 7 is a view illustrating a state where the distal end rigid part 116 related to the first embodiment is seen from the front (subject side), and is a view corresponding to the configuration of FIG. 3. In the first embodiment, an optical axis L1 of the measurement auxiliary light and an optical axis L2 of the imaging optical system are present on the same plane and intersect each other on the same plane. Hence, in a case where the distal end rigid part 116 is seen from the front (subject side), as illustrated in FIG. 7, the optical axis L2 appears to pass on the optical axis L1. In addition, FIG. 8 is a view corresponding to the configuration of FIG. 4. Also in the aspect illustrated in FIGS. 4 and 8, the optical axis L1 of the measurement auxiliary light and the optical axis L2 of the imaging optical system are present on the same plane and intersect each other on the same plane. According to these aspects, since the optical axis L2 of the imaging optical system and the optical axis L1 of the measurement auxiliary light are present on the same plane and a track of the marker accompanying an observation distance change passes through the center of a screen, a region where the marker is present in the vicinity of the center of the screen becomes wide, and the measurement accuracy is improved.

Figure 9:
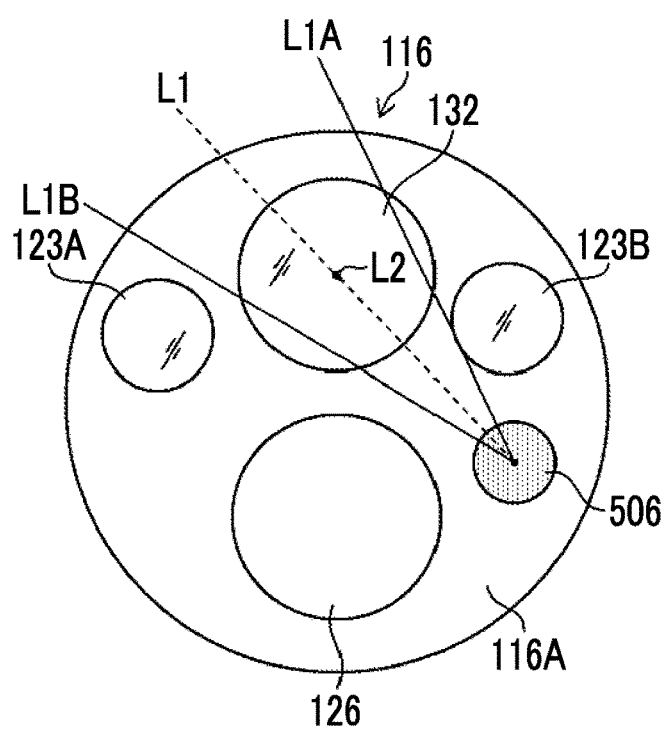
FIG. 9 is still another view illustrating the relationship between the optical axis of the imaging optical system and the optical axis of the measurement auxiliary light.

In addition, the relationship between the optical axis L1 of the measurement auxiliary light and the optical axis L2 of the imaging optical system in the invention may be limited to the above-described aspect in which "the optical axis of the measurement auxiliary light and the optical axis of the imaging optical system are present on the same plane and intersect each other on the same plane", and the optical axis of the measurement auxiliary light may not be present on the same plane as the optical axis L2 of the imaging optical system, as in optical axes L1A and L1B illustrated in FIG. 9. However, even in such a case, in a case where the optical axis of the measurement auxiliary light is projected on the plane including the optical axis of the imaging optical system, the optical axis of the measurement auxiliary light has the inclination angle, which is not 0 degrees with respect to the optical axis of the imaging optical system, and crosses the field angle of the imaging optical system.

In a case where the optical axis of the measurement auxiliary light is parallel to the optical axis of the imaging optical system (the inclination angle is 0 degrees) as in the above-described JP1996-285541, the distance up to a point where the optical axis of the measurement auxiliary light crosses the field angle of the imaging optical system becomes long depending on the spacing between the optical axes. In that case, a spot cannot be imaged in a closest range, and the measurement is difficult. Additionally, in a case where the optical axis of the measurement auxiliary light is parallel to the optical axis of the imaging optical system, there is a case where the sensitivity of a spot position change with respect to a change in observation distance is low and sufficient measurement accuracy is not obtained. In contrast, according to the configuration in which, "in a case where the optical axis of measurement auxiliary light is projected on the plane including the optical axis of the imaging optical system, the optical axis of the measurement auxiliary light has the inclination angle, which is not 0 degrees with respect to the optical axis of the imaging optical system, and crosses the field angle of the imaging optical system" as in the first embodiment, the measurement can be made at an observation distance of a wide range from the closest range to a long range. Additionally, since the sensitivity of the spot position change with respect to the distance change is high, the measurement can be made with high accuracy.

<Configuration of Light Source Device>

As illustrated in FIG. 2, the light source device 300 is constituted of a light source 310 for illumination, a stop 330, a condensing lens 340, a light source control unit 350, and the like, and makes illumination light (the visible light or infrared light) incident on the light guide 170. The light source 310 includes a visible light source 310A and an infrared light source 310B, and is capable of radiating one or both of the visible light and the infrared light. The illuminance of the illumination light by the visible light source 310A and the infrared light source 310B is controlled by the light source control unit 350, and as will be described below, is capable of lowering the illuminance of the illumination light as necessary or stopping the illumination, in a case where a spot is imaged and measured (in the measurement mode).

By coupling the light guide connector 108 (refer to FIG. 1) to the light source device 300, the illumination light radiated from the light source device 300 is transmitted to the illuminating lenses 123A and 123B via the light guide 170 and is radiated to an observation range from the illuminating lenses 123A and 123B.

<Configuration of Endoscope Processor>

Next, the configuration of the endoscope processor 200 will be described with reference to FIG. 2. The endoscope processor 200 inputs the image signals output from the endoscope device 100 via an image input controller 202, and performs image processing required by an image processing unit 204 to outputs the image signals via a video output unit 206. Accordingly, an observation image is displayed on the monitor 400. These kinds of processing are performed under the control of a central processing unit (CPU) 210. In the image processing unit 204, switching and overlap display of images displayed on the monitor 400, electronic zooming processing, display of images according to operation modes, extraction of a specific component (for example, a luminance signal) from the image signals, and the like are performed in addition to image processing, such as white balance adjustment. Additionally, in the image processing unit 204, measurement of a spot position on the imaging surface of the imaging element 134 and calculation of the size (the number of pixels) of a marker based on the measured position are performed (to be described below). Information required for the processing performed by the CPU 210 or the image processing unit 204, for example, a relationship between the position of a spot and the size of a marker on the imaging surface of the imaging element 134 is stored in advance in a memory 212. This relationship may be stored in a function form or may be stored in a table form.

Additionally, the endoscope processor 200 includes the operating part 208. The operating part 208 includes an operation mode setting switch, a water supply instruction button, and the like that are not illustrated, and is capable of operating radiation of the visible light and/or the infrared light. The operating part 208 further includes a keyboard and a mouse (selection unit; not illustrated) that receive user's operations, and the user can operate switching of observation modes, display condition setting of markers, and the like with these devices.

<Observation by Endoscope Device>

Figure 10:
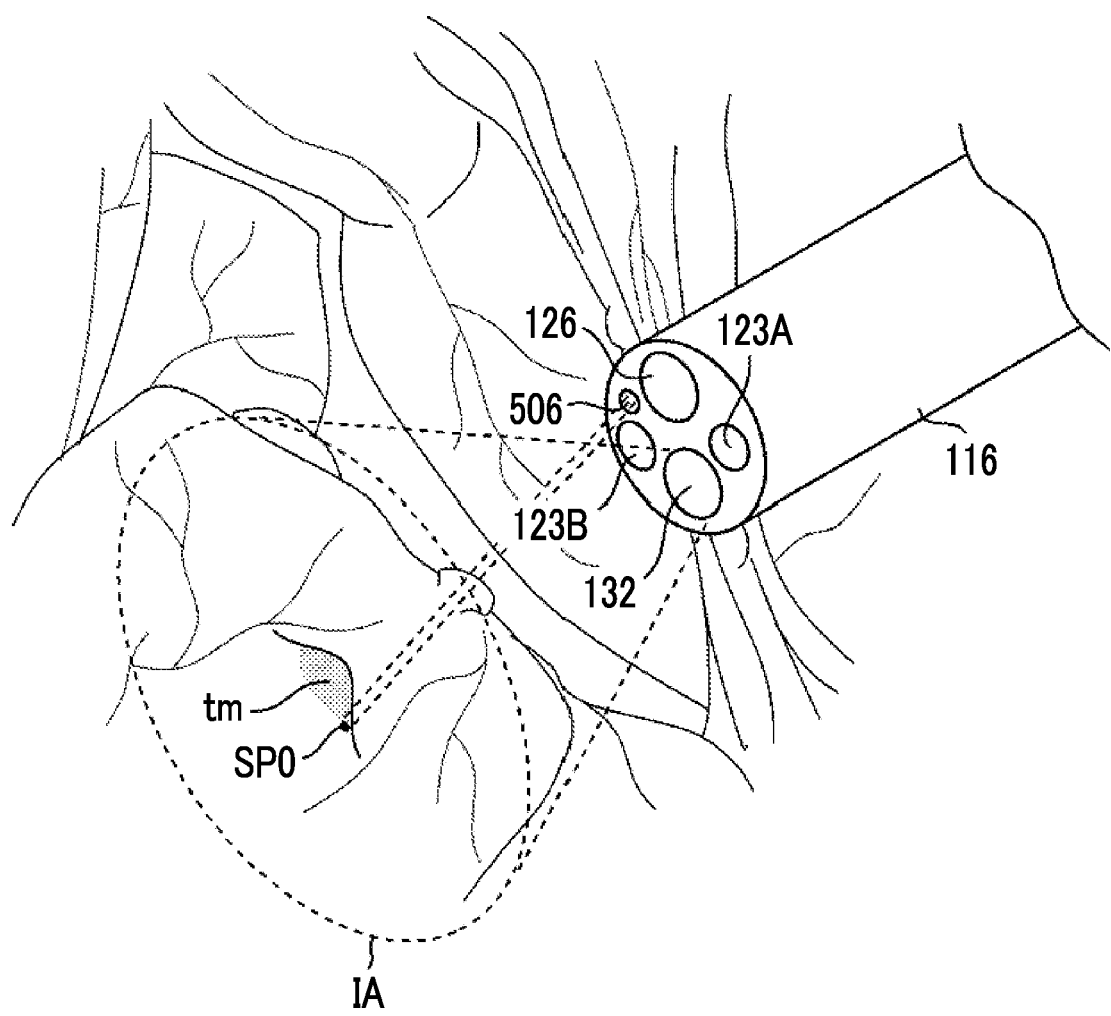
FIG. 10 is a view illustrating a state where an insertion part of an endoscope is inserted into a test object.

FIG. 10 is a view illustrating a state where the insertion part 104 of the endoscope device 100 is inserted into the test object, and illustrates a state where an observation image is acquired regarding an imaging range IA via the imaging optical system 130. FIG. 10 illustrates a state where a spot SP0 is formed in the vicinity of a tumor tm (a portion that bulges in black).

<Flow of Measuring Processing>

Figure 11:
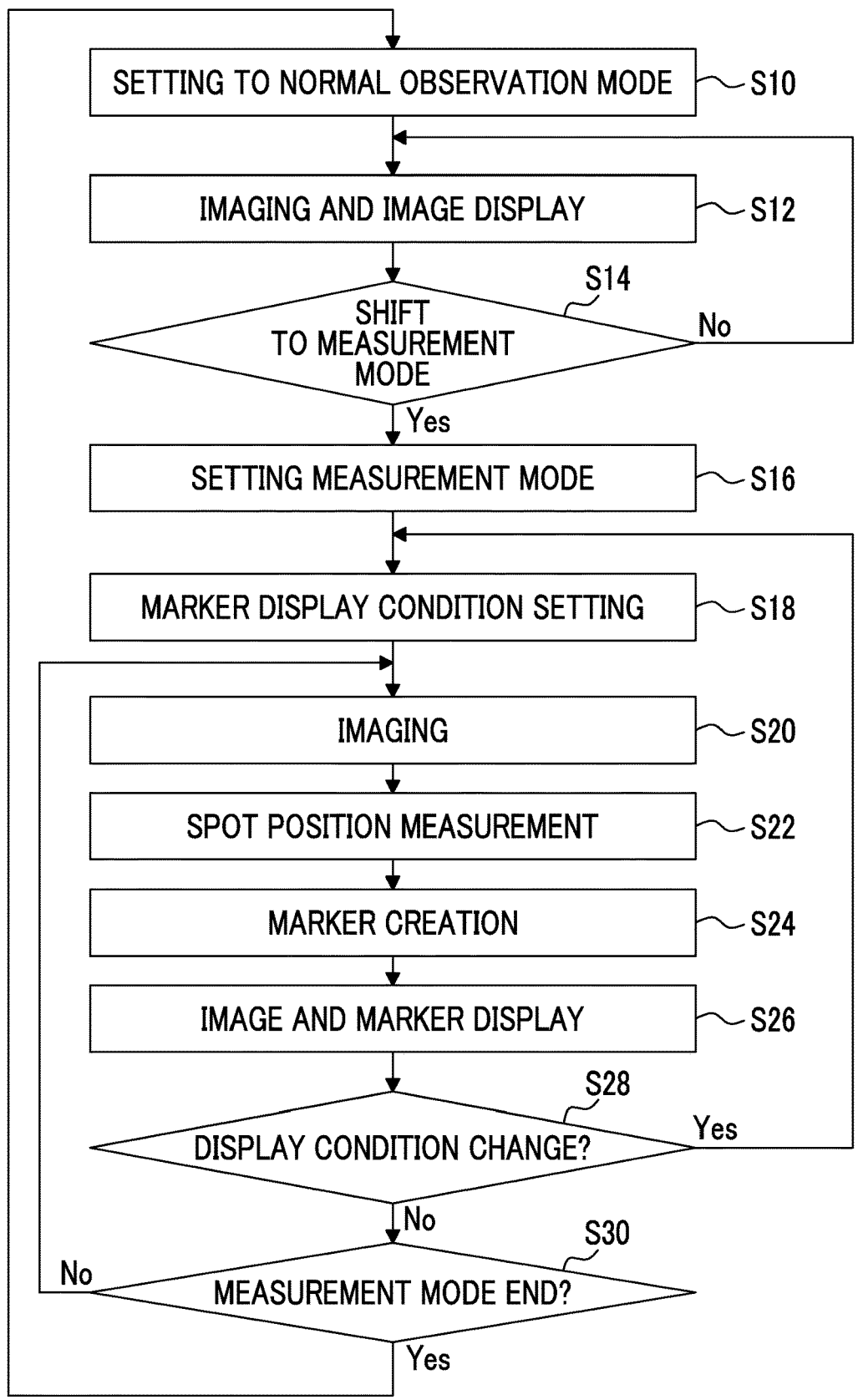
FIG. 11 is a flowchart illustrating a measurement procedure.

Next, the measurement of the test object using the endoscope system 10 will be described. FIG. 11 is a flowchart illustrating measurement processing.

First, the insertion part 104 of the endoscope device 100 is inserted into the test object, and the endoscope system 10 is set to a normal observation mode (Step S10). The normal observation mode is a mode in which the subject is irradiated with the illumination light radiated from the light source device 300 to acquire an image and the subject is observed. The setting to the normal observation mode may be automatically performed by the endoscope processor 200 at the time of the startup of the endoscope system 10 or may be performed in accordance with the operation of the operating part 208 and/or a touch panel of the monitor 400 by a user.

In a case where the endoscope system 10 is set to the normal observation mode, the illumination light is radiated to image the subject, and the obtained image displayed on the monitor 400 (Step S12). As the image of the subject, a still image may be captured or a moving image may be captured. During the imaging, it is preferable to switch the type (the visible light or the infrared light) of the illumination light in accordance with the type of the subject or the purposes of observation. The user moves the insertion part 104 forward or backward and/or operates to bend the insertion part 104 to direct the distal end rigid part 116 to an observation target while viewing an image displayed on the monitor 400 so that the subject to be measured (a specific region, such as an affected region) can be imaged.

Next, whether or not the normal observation mode shifts to a measurement mode is determined (Step S14). This determination may be performed on the basis of the presence or absence of a user's operation via the operating part 208 and/or the touch panel of the monitor 400, or may be performed on the basis of the presence or absence of a switching command from the endoscope processor 200. Additionally, the endoscope processor 200 may alternately set the normal observation mode and the measurement mode at fixed frame intervals (such as every one frame or every two frames). In a case where the determination of Step S14 is negative, the process returns to Step S12 and the imaging in the normal observation mode is continued, and in a case where the determination is positive, the process proceeds to Step S16 where switching to the measurement mode is performed.

The measurement mode is a mode in which the laser light (measurement auxiliary light) is radiated from the laser head 506 to form a spot on the subject, and a marker for measuring the size (length) of the subject on the basis of the image of the subject on which the spot is formed is created and displayed. In the first embodiment, the red laser light is used as the measurement auxiliary light. Thus, since much of a digestive tract is reddish in an endoscopic image, there is a case where the spot is not easily recognized depending on measurement conditions. Thus, in the measurement mode, in Step S16, the illumination light is turned off during the image acquisition and the position measurement of the spot, or the illuminance is lowered to such a degrees that the recognition of the spot is not affected, and the measurement auxiliary light is radiated from the laser head 506. Such control can be performed by the endoscope processor 200 and the light source control unit 350.

<Setting of Marker Display Condition>

Display conditions of the marker (index figure) are set in Step S18. This setting can be performed by the endoscope processor 200 through user's operations via the operating part 208 and/or the touch panel of the monitor 400. Accordingly, the user can display the marker in desired modes and can easily measure the size of the subject. The details of the display condition setting operation will be described below (refer to FIGS. 16 to 30). In addition, in the flowchart of FIG. 11, after the measurement mode setting in Step S16, marker display conditions are set. However, the setting of the display conditions may be performed at other timings, such as at system startup. Additionally, the display conditions can be changed as necessary (refer to Step S28).

In Step S20, an image of the subject (a specific region, such as an affected region) on which the spot is formed with the measurement auxiliary light is captured. In a case where the observation distance is within a measurement range, the spot is formed within the imaging field angle of the imaging optical system 130. As will be described in detail below, the positions of spots within an image (on the imaging element) are different in accordance with the observation distance, and the sizes (the numbers of pixels) of markers to be displayed are different in accordance with the positions of the spots.

<Changes in Spot Position According to Observation Distance>

Figure 12:
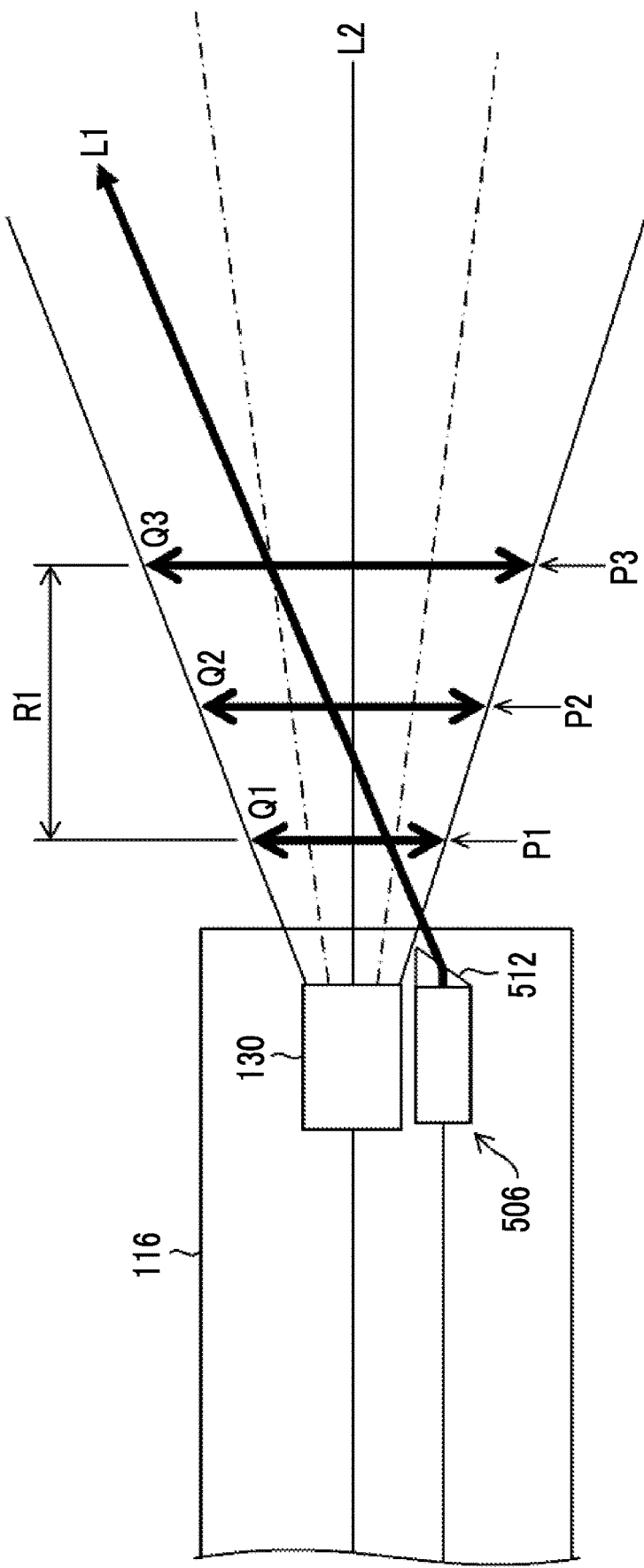
FIG. 12 is a view illustrating a state where the optical axis of the measurement auxiliary light crosses the imaging view angle of the imaging optical system.

In the first embodiment, in a case where the optical axis L1 of the measurement auxiliary light is projected on the plane including the optical axis L2 of the imaging optical system, the optical axis L1 has the inclination angle, which is not 0 degrees with respect to the optical axis L2, and crosses the field angle of the imaging optical system. Hence, the positions of spots in an image (imaging element) are different depending on distances up to subjects. For example, as illustrated in FIG. 12 (a view illustrating a state where the distal end rigid part 116 is seen from a lateral direction within the plane including the optical axis L1 and the optical axis L2), supposing that observation is possible in a range R1 (length measurement distance range) of the observation distance, at a near end P1 (closest range), a point P2 in the vicinity of the center, and a far end P3 (longest range) in the range R1, it can be understood that the positions of spots in imaging ranges (indicated by arrows Q1, Q2, and Q3) at the respective points (points where the respective arrows and the optical axis L1 intersect each other) are different. In addition, in FIG. 12, the inside of solid lines is the imaging view angle of the imaging optical system 130, and the inside of one-dot chain lines is a measurement field angle. Measurement is performed at a central portion with small aberration among the imaging view angle of the imaging optical system 130.

Figure 13:
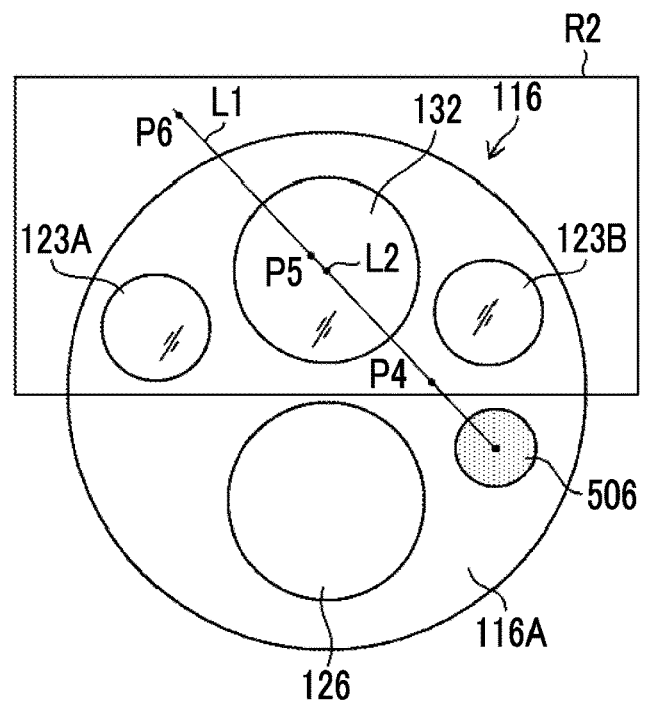
FIG. 13 is a view illustrating a state where a spot position varies depending on an imaging distance.

FIG. 13 is a view illustrating a state where the distal end rigid part 116 is seen from the front similarly to FIG. 7, and is a view virtually illustrating a relationship between the optical axis L1 of the imaging optical system 130, the optical axis L2 of the measurement auxiliary light, and an imaging range R2 of the imaging element 134. FIG. 13 illustrates a case where the optical axes L1 and L2 are present on the same plane and intersect each other on the plane. In an example of FIG. 13, spot positions P4, P5, and P6 (corresponds to cases where the observation distance is in the vicinity of the near end, in the vicinity of the center, and in the vicinity of the far end, respectively) formed at positions according to the observation distance are illustrated. In addition, in a case where the laser head 506 is provided in the forceps port 126 (refer to FIG. 8), as illustrated in FIG. 14, spots P7, P8, and P9 (correspond to cases where the observation distance is in the vicinity of the near end, in the vicinity of the center, and in the vicinity of the far end, respectively) are obtained in an imaging range R3.

Figure 14:
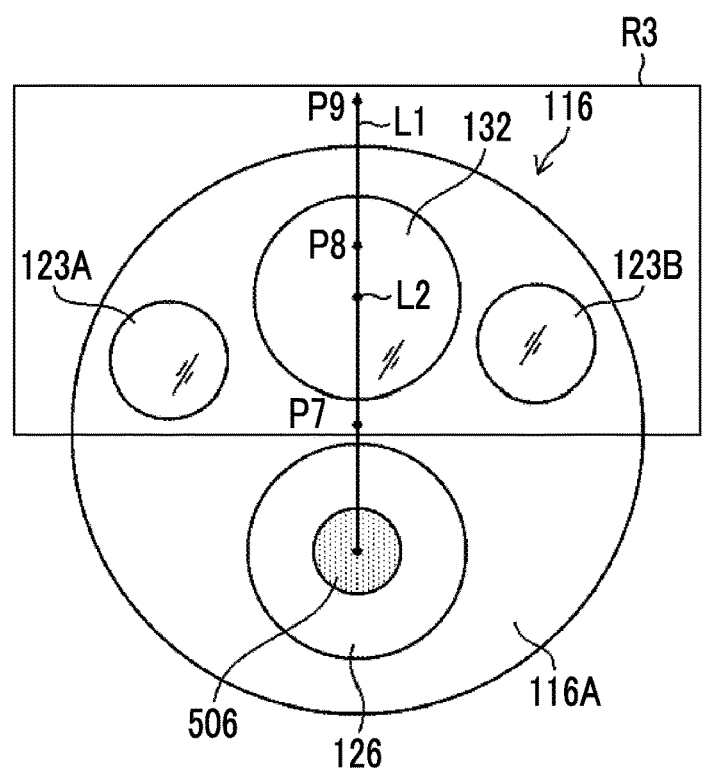
FIG. 14 is another view illustrating a state where the spot position varies depending on the imaging distance.

As illustrated in FIGS. 13 and 14, it can be understood that a spot position in a case where the observation distance is in the vicinity of the far end (longest range) and a spot position in a case where the observation distance is in the vicinity of the near end (closest range) are located opposite to each other with the optical axis L1 of the imaging optical system 130 interposed therebetween.

In the related-art technique as described in the above-described JP1996-285541 in contrast with the changes in spot position in such a first embodiment, since the optical axis of the measurement auxiliary light is parallel to the optical axis of the imaging optical system, the movement of the spot positions resulting from changes in the observation distance is small. Specifically, in a case where the observation distance is short, spots are present at positions apart from the center (the center of the imaging element) of a captured image and approach the center (the center of the imaging element) of the captured image as the observation distance becomes longer. However, the spot positions are not located on the opposite sides of the optical axis of the imaging optical system at the near end and the far end of the observation distance. In contrast to such a related-art technique, in the first embodiment, the sensitivity of the movement of the spot positions with respect to the changes in the observation distance is high as described above, and the sizes of subjects can be measured with high accuracy.

In this way, although the spot positions within the captured image (on the imaging element 134) are different in accordance with the relationship between the optical axis L2 of the imaging optical system 130 and the optical axis L1 of the measurement auxiliary light, and the observation distance. However, the number of pixels indicating the same actual size (for example, 5 mm) increases in a case where the observation distance is near, and the number of pixels decreases in a case where the observation distance is far. Hence, as will be described in detail below, the sizes of markers can be calculated by storing information indicating a relationship between the positions of spots and the sizes (the numbers of pixels) of markers corresponding to actual sizes of subjects in advance and acquiring this information according to the spot positions. In addition, it is not necessary to measure the observation distance itself at the time of calculation.

Figure 15:
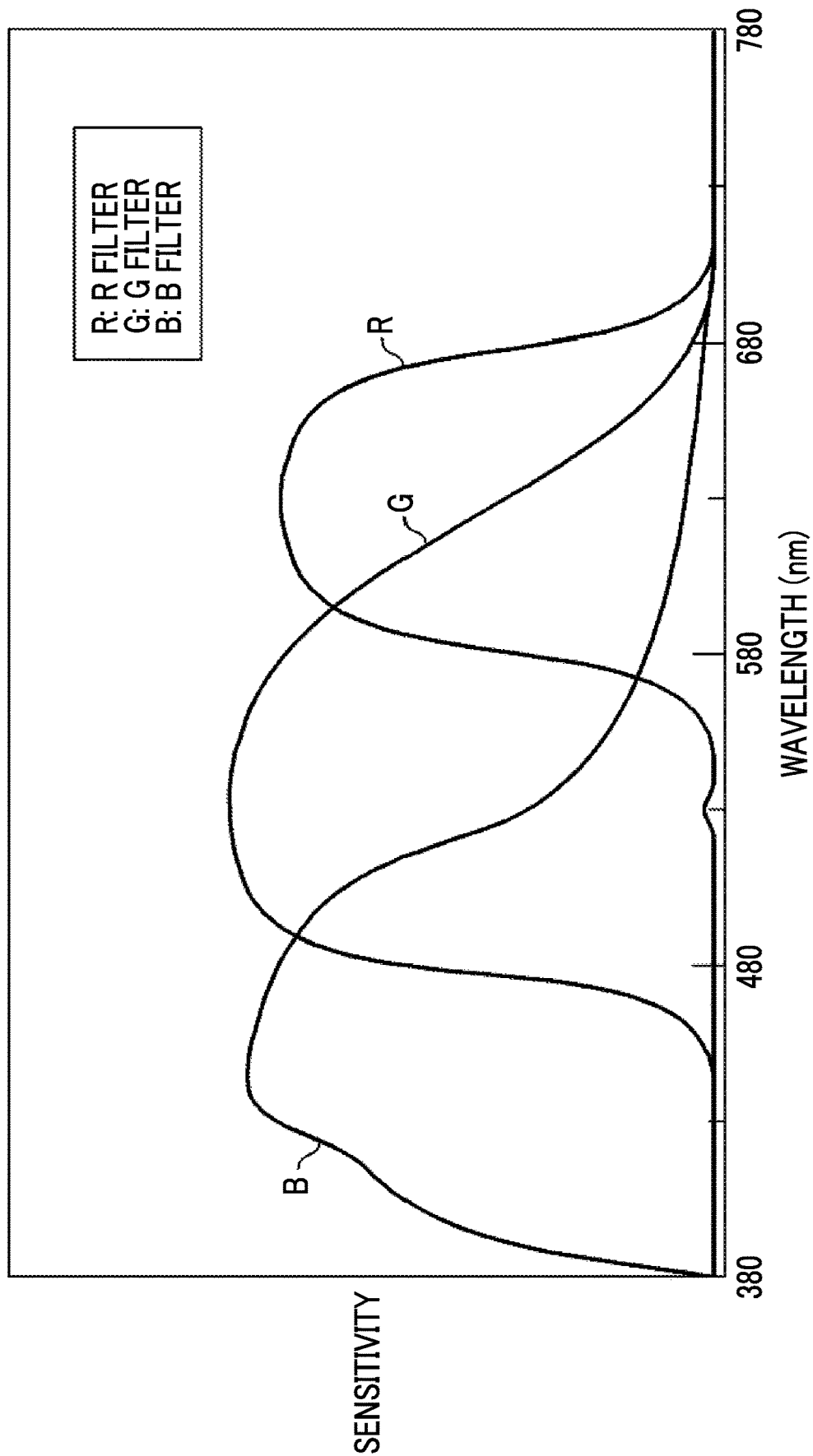
FIG. 15 is a view illustrating a relationship between wavelength and the sensitivity of color filters.

Referring to the flowchart of FIG. 11, the position measurement (Step S22) of the spot on the imaging surface of the imaging element 134 will be described. The position measurement of the spot in Step S22 is performed by an image created by pixel signals of pixels in which color filters of a filter color of a red (R) color are disposed. Here, a relationship between the wavelength and sensitivity in color filters of respective colors (red, green, and blue) disposed in respective pixels of the imaging element 134 is as illustrated FIG. 15. Additionally, the laser light emitted from the laser head 506 is red laser light with a wavelength of 650 nm. That is, the measurement of the spot position is performed on the basis of the image created by the image signals of the pixels (R pixels) in which color filters of a red color with the highest sensitivity with respect to the wavelength of the laser light among color filters of red, green, and blue are disposed. In this case, the position of the spot can be recognized at high speed by providing a threshold value to the signal intensity of R pixels of bit map data or raw image format (RAW) data of the pixel signals to perform binarization and calculating the center of gravity of a white portion (a pixel having a higher signal intensity than the threshold value). In addition, in a case a spot is recognized by an actual image (an image created by pixel signals of all colors), it is preferable that pixel signals of pixels (G pixels and B pixels) in which green and blue color filters are disposed are provided with threshold values, and pixels in which values of the pixel signals of the G pixels and the B pixels having the bit map data are equal to or smaller than the threshold values are extracted.

In addition, the above-described technique is an example of the spot position measurement, and other well-known techniques may be adopted regarding the image recognition and the spot recognition.

In addition, in the measurement mode, as described above, the illumination light is turned off during the image acquisition (Step S20) and the position measurement (Step S22) of the spot, or the illuminance is lowered to such a degrees that the recognition of the spot is not affected, and the measurement auxiliary light is radiated from the laser head 506. In a case where the illuminance of the illumination light in imaging the spot is too high, there is a case where the contrast between the spot and portions other than the spot becomes small in an obtained image, recognition of the spot cannot be performed, and measurement becomes impossible. However, an image with a clear spot can be acquired by turning off or dimming the illumination light as necessary in this way, and a marker with a suitable size can be created and displayed by accurately measuring the position of the spot. In addition, the illumination light is not necessarily dimmed or turned off, and the illuminance remains as it is in a case where the recognition of the spot is not affected.

In Step S24, a marker indicating the actual size of the subject is created. As described above, since the sizes of markers are different in accordance with the positions of spots within an image (namely, on the imaging surface of the imaging element), the relationship between the positions of the spots and the sizes (the numbers of pixels) of the markers corresponding to the actual sizes of the subjects are measured in advance, information indicating the relationship is stored in the memory 212, the endoscope processor 200 acquires information from the memory 212 in accordance with the spot position measured in Step S22 and finds the size of the marker on the basis of the acquired information. By performing the processing of Step S22 and S24 whenever the imaging is performed in Step S20, the size of the marker can be set in accordance with the position of the spot on the imaging element 134. In addition, it is preferable that the sizes of markers are set in real time. However, in a case where a demand for a real-time property of the measurement is not high, the sizes of the markers may be found not in real time (whenever the imaging is performed in Step S20) but at every certain frame interval (as a result, there may be a slight delay in the imaging and the size calculation of the markers), and in a case where there is a user's designation, the size of the marker may be found. Additionally, in a case where the measurement may not be performed in real time, required imaging and required recording of an image may be performed, and then, the creation and the display of the markers may be separately performed (off-line or the like).

A procedure of finding a relationship between spot positions and the sizes of markers, and the operation of setting the display conditions of the markers will be described in detail below.

In Step S26, the observation image and the marker are displayed on the monitor 400. In the endoscope system 10 related to the first embodiment, the size of a specific region size can be easily measured from the displayed marker. The display condition setting of markers and the display based on the basis of the set conditions will be described in detail below (see FIGS. 16 to 30).

In Step S28, it is determined whether or not the display conditions of the marker are changed. This determination can be performed on the basis of a user's operation via the operating part 208 and/or the monitor 400. In a case where the determination is positive, the process returns to Step S18 where the display conditions are set again, and in a case where the determination is positive, the process proceeds to Step S30 where whether or the measurement mode is ended is determined. The determination in Step S30 may be performed on the basis of a user's operation via the operating part 208 and/or the monitor 400, or may be performed on the basis of the presence or absence of a switching command from the endoscope processor 200. Additionally, similarly to during the shift to the measurement mode, in a case where a certain number of frames have elapsed, the measurement mode may be automatically ended and may return to the normal observation mode. In a case where the determination of Step S30 is negative, the process returns to Step S20 and the processing of Step S20 to Step S28 is repeated. In a case where the determination of Step S30 is positive, the measurement auxiliary light is turned off, the illuminance of the illumination light is returned to normal illuminance, and the process returns to the normal observation mode (returns to Step S10). In addition, in a case where there is no hindrance in the observation in the normal observation mode, the measurement auxiliary light may not be turned off.

<Setting of Marker Display Condition>

Next, the above-described marker display condition setting (Step S18 of FIG. 11) and display modes according to set conditions will be described in detail. FIG. 16 is a view illustrating an example of an initial screen for setting the marker display conditions. In FIG. 16, condition names (Regions C01 to C08), setting condition contents (numerical values and the like; Regions V01 to V08), and condition setting buttons (A01 to A08) are illustrated for respective display condition items. Button B01 provided at a lower part of the screen is a button for confirming the display conditions, Button B02 is a button for cancelling condition changes, and Button B03 is a button for clearing condition changes (returning to initial values). Screens of FIGS. 16 to 30 are displayed on the monitor 400, and the display conditions can be set by user's operations via the touch panel of the monitor 400 and/or a keyboard and a mouse (not illustrated) of the operating part 208.

Regions C01 and V01 indicate the number of markers to be displayed, and one or a plurality of markers can be displayed by a selection operation via Button A01. Regions C02 and V02 indicate the shape of a marker, and markers, such as a cross, a graduated cross, a point, a circle, and a circle and cross, can be displayed by an operation via Button A02. Regions C03 and V03 indicate the size (actual size) of a marker, and a specific numerical value (for example, 5 mm) can be selected by an operation via Button A03. Regions C04 and V04 indicate the color of a marker, and colors, such as white, black, red, and blue, can be selected by a selection operation via Button A04. Regions C05 and V05 indicate whether or not a specific value (for example, 5 mm) of the size of a marker is displayed with the marker, and whether or not the specific value is displayed can be selected by an operation via Button A05 (ON or OFF). Regions C06 and V06 indicate whether or not a marker is distorted and displayed according to the distortion aberration of the imaging optical system 130, and whether or not the marker is distorted and displayed (ON or OFF) can be selected by a selection operation via Button A06. Regions C07 and V07 indicate whether or not the center of a marker is made to coincide with the center of a spot and displayed, and whether or not the center of the marker and the center of the spot are made to coincide with each other and displayed (ON or OFF) can be selected by an operation via Button A07. Region C08 and V08 indicate whether or not graduations are displayed on a marker (for example, the graduations are displayed every 2 mm in a case where the size of the marker is 10 mm), and whether or not the graduations are displayed (ON or OFF) can be selected a selection operation via Button A08.

<Specific Example of Display Condition Setting>

Next, specific examples of the display condition setting operation will be described. FIG. 17 is a view illustrating an example of a screen where the number of markers is set. In a case where Button A01 is designated by the operation of the touch panel provided in the monitor 400 on the screen of FIG. 16, the operation (the same applies to the other items) via the operating part 208, or the like, region V01 is brought into a pull-down display state and shifts to the state of FIG. 17. In addition, illustration of items other than the number of markers is omitted in FIG. 17. In FIG. 17, values (in this case, from 1 to 5) capable of being set as the number of markers are displayed on Region V01. In order to set a value, the user may move a selection range up and down with Buttons A01a and A01b, and Slide Bar A01c to select a numerical value (Example 1 "1"), and designate Button B01 (OK button).

FIG. 18 is a view illustrating an example of a screen where the shape of a marker is set. In a case where Button A02 is designated on the screen of FIG. 16, Region V02 is brought into a pull-down display state and shifts to the state of FIG. 18 (illustration of items other than the marker shape is omitted). As described above, since 1 is set as the number of markers in Example 1, the marker shape may be set for one marker. In Example 1, the marker shape can be selected from "Cross, Graduated cross, Point, Circle, and Circle and Cross". Similarly to FIG. 17, the user may move a selection range up and down with Buttons A02a and A02b and Slide Bar A02c to select a shape ("Cross" in Example 1), and designate Button B01.

FIG. 19 is a view illustrating an example of a screen where the size (actual size) of a marker is set. In a case where Button A03 is designated on the screen of FIG. 16, Region V03 is brought into a pull-down display state and shifts to the state of FIG. 19 (illustration of items other than the size is omitted). As described above, since 1 is set as the number of markers in Example 1, the size of a marker may be set for one marker. In Example 1, the size of a marker can be selected "2 mm, 3 mm, 5 mm, 7 mm, and 10 mm". Similarly to FIG. 17, the user may move a selection range up and down with Buttons A03a and A03b and Slide Bar A03c to select a size ("5 mm" in Example 1), and designate Button B01. In addition, "the size of a marker is 5 mm" means that "a marker of a size (the number of pixels) corresponding to 5 mm in actual size is displayed on the screen of the monitor 400", and the size of the marker on the screen of the monitor 400 does not need to be 5 mm.

FIG. 20 is a view illustrating an example of a screen where the color of a marker is set. In a case where Button A04 is designated on the screen of FIG. 16, Region V04 is brought into a pull-down display state and shifts to the state of FIG. 20 (illustration of items other than the color is omitted). As described above, since 1 is set as the number of markers in Example 1, the color of a marker may be set for one marker. In Example 1, the marker color can be selected from "Red, Blue, White, Black, Yellow, and Green". Similarly to FIG. 17, the user may move a selection range up and down with Buttons A04a and A04b and Slide Bar A04c to select a color ("Black" in Example 1), and designate Button B01.

Figure 30:
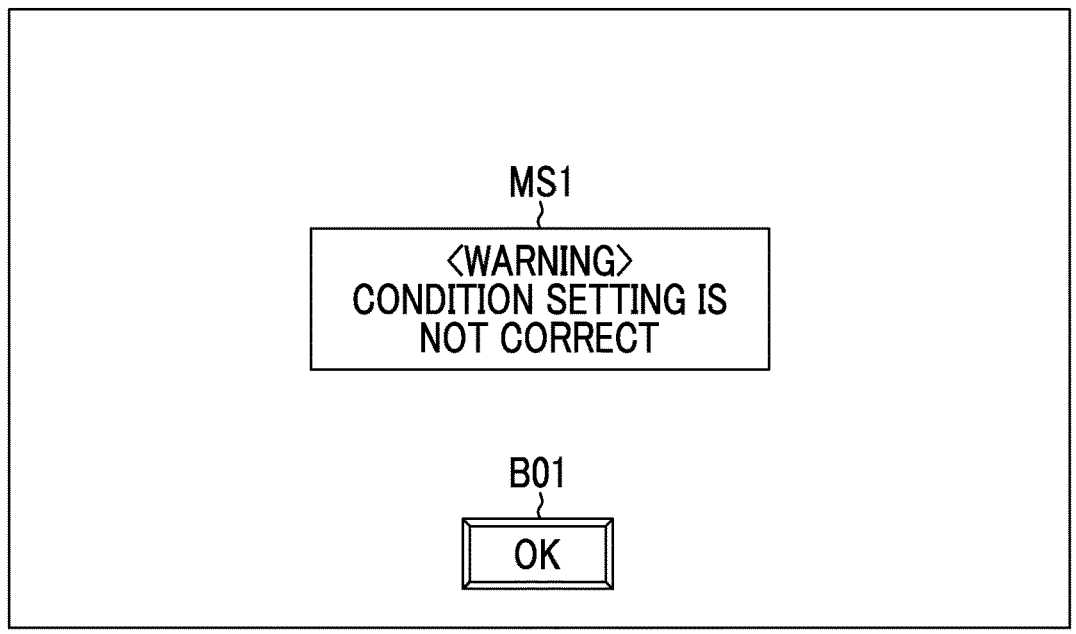
FIG. 30 is a view illustrating an example of a warning message against marker display conditions.

By the above-described operations, the conditions of "Number of markers: 1, Shape: Cross, Color: Black, and Size: 5 mm" are set. Additionally, by the similar operations, it is assumed that the conditions of "Numeral Display: ON, Offset Display: OFF, and Distortion Display: OFF" are set. In addition, in a case where there is mismatching (for example, a number set in "Number of Markers" is different from a number in set in "Size") between the display conditions set by the user, as illustrated in FIG. 30, a warning message MS1 may be output.

<<Setting of Display Conditions by Other Operating Means>>

In the above-described example, a case where the marker display conditions are set by the touch panel of the monitor 400 and/or the keyboard and the mouse (not illustrated) of the operating part 208 has been described. However, the setting of the display conditions may be performed via other operating means. For example, buttons may be provided on the proximal operating part 102 to set the display conditions. Additionally, the display conditions may be set by a foot pedal, an audio input, a sight line input, a gesture input, and the like. There is a case where the user is unable to freely move both hands during the operation of the endoscope device 100. In such a case, the operating means are effective.

In a case where the display conditions are set, specific values may be stepwise switched user's operations. For example, stepwise switching resulting from button operation of the proximal operating part 102, a foot pedal, voice, and the like may be performed. An example of such stepwise switching may include an aspect in which, whenever the operating means is operated, the size of a marker is changed to "2 mm-3 mm-4 mm-5 mm-7 mm-10 mm-15 mm-20 mm-30 mm-50 mm-2 mm . . . (repeated in the following)".

<Specific Examples of Screen Display>

Example 1

Figure 21:
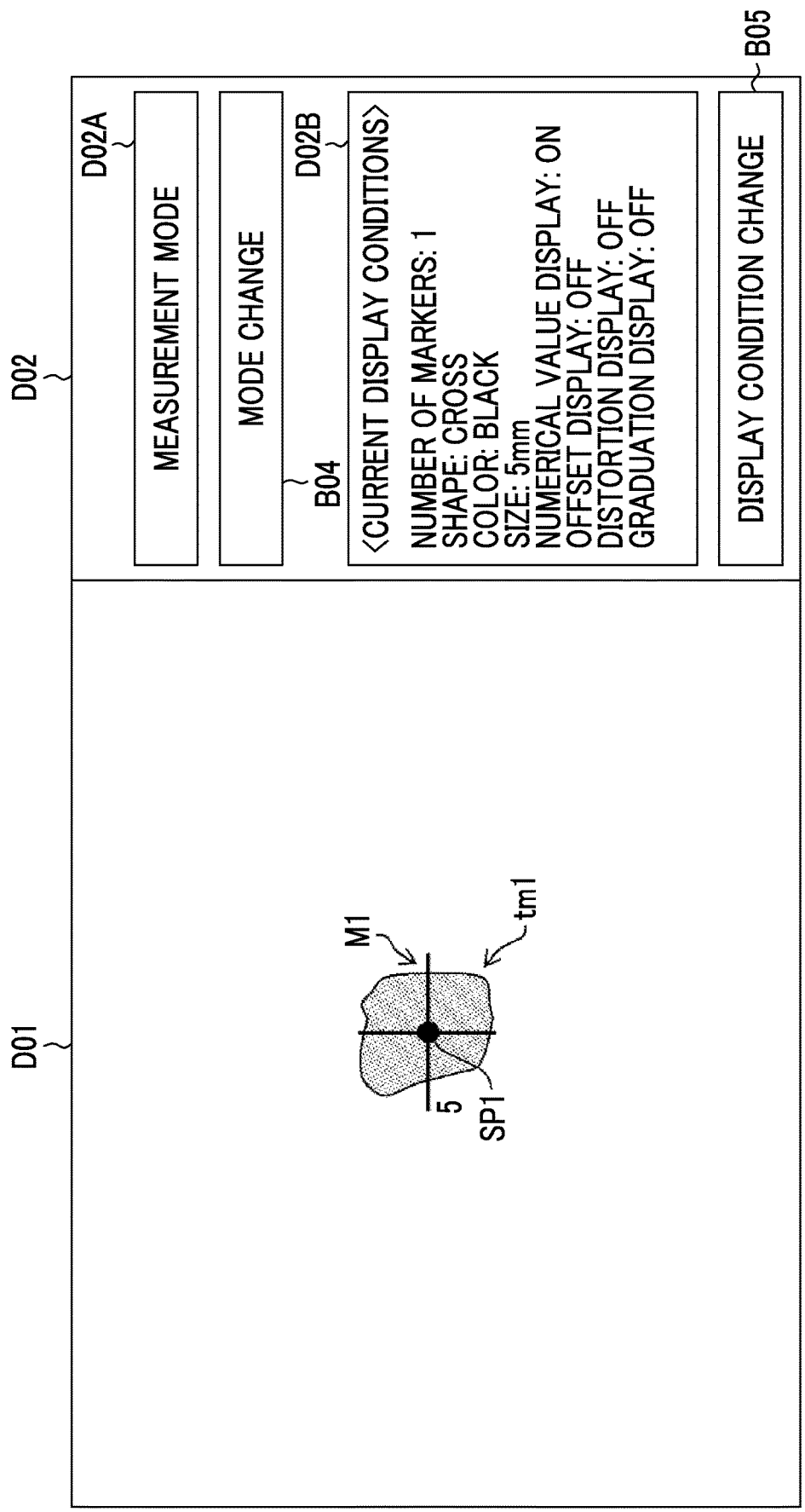
FIG. 21 is a view illustrating a state where a spot formed in a tumor and a cross-shaped marker having the spot as a center are displayed.
Figure 22:
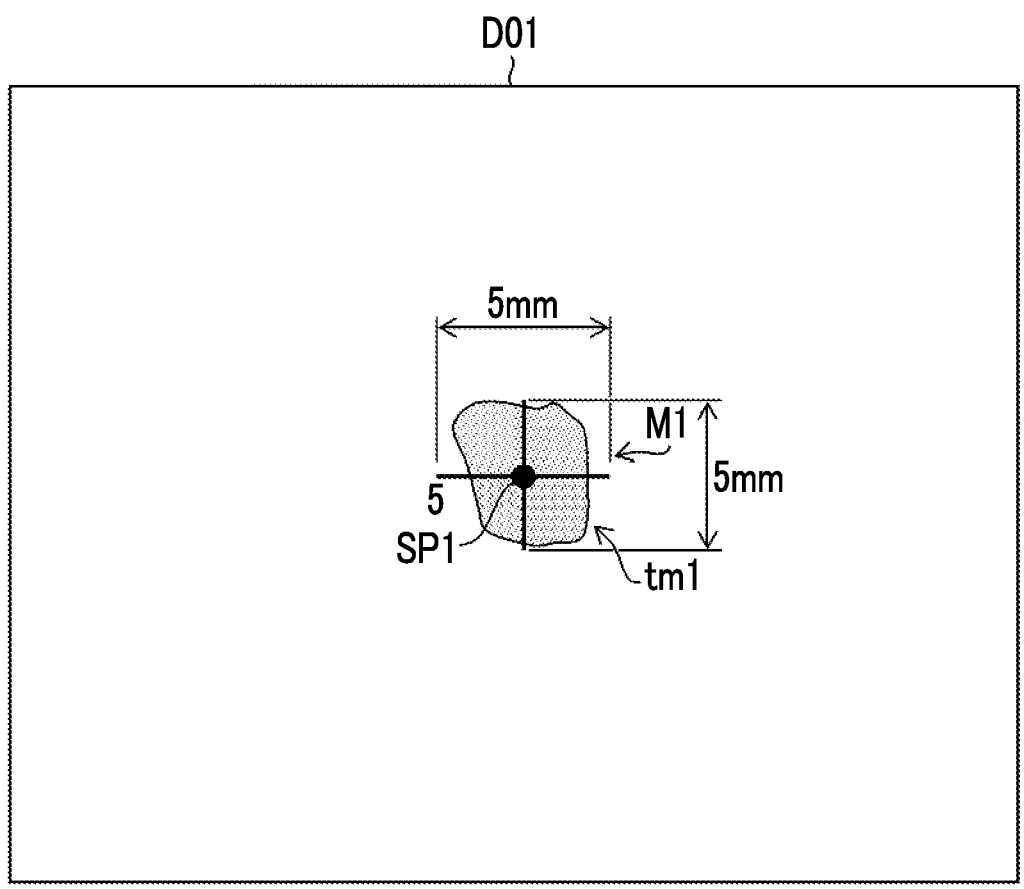
FIG. 22 is a view for explaining the size of the marker.

An example of the screen display on the above-described conditions is illustrated in FIG. 21. As illustrated in FIG. 21, a screen displayed on the monitor 400 is constituted of an image display region D01 and an information display region D02. In the image display region D01, a spot SP1 is formed with respect to a tumor tm1, and a cross-shaped marker M1 (single marker) is displayed in black with the center thereof being made to coincide with the spot SP1. That it is, "5" in FIG. 21 indicates that, as illustrated in FIG. 22, the size of the marker M1 (the number of pixels) on the screen in an upward-downward direction and leftward-rightward direction corresponds to 5 mm in actual size. Meanwhile, in the information display region D02, the fact that the endoscope system 10 is in "Measurement Mode" is displayed on a region D02A, and current display conditions are displayed on a region D02B. In a case where Button B04 is designated, a change to the normal observation mode is made, and in a case where Button B05 is designated, the display condition setting screens as illustrated in FIGS. 16 to 20 are displayed.

The display conditions can be easily checked and/or changed by the above-described information display region D02. In addition, the information display region D02 may be a separate screen, or the image display region D01 may be widened, for example, by hiding, reducing, or the like in the observation modes.

Example 2

Figure 23:
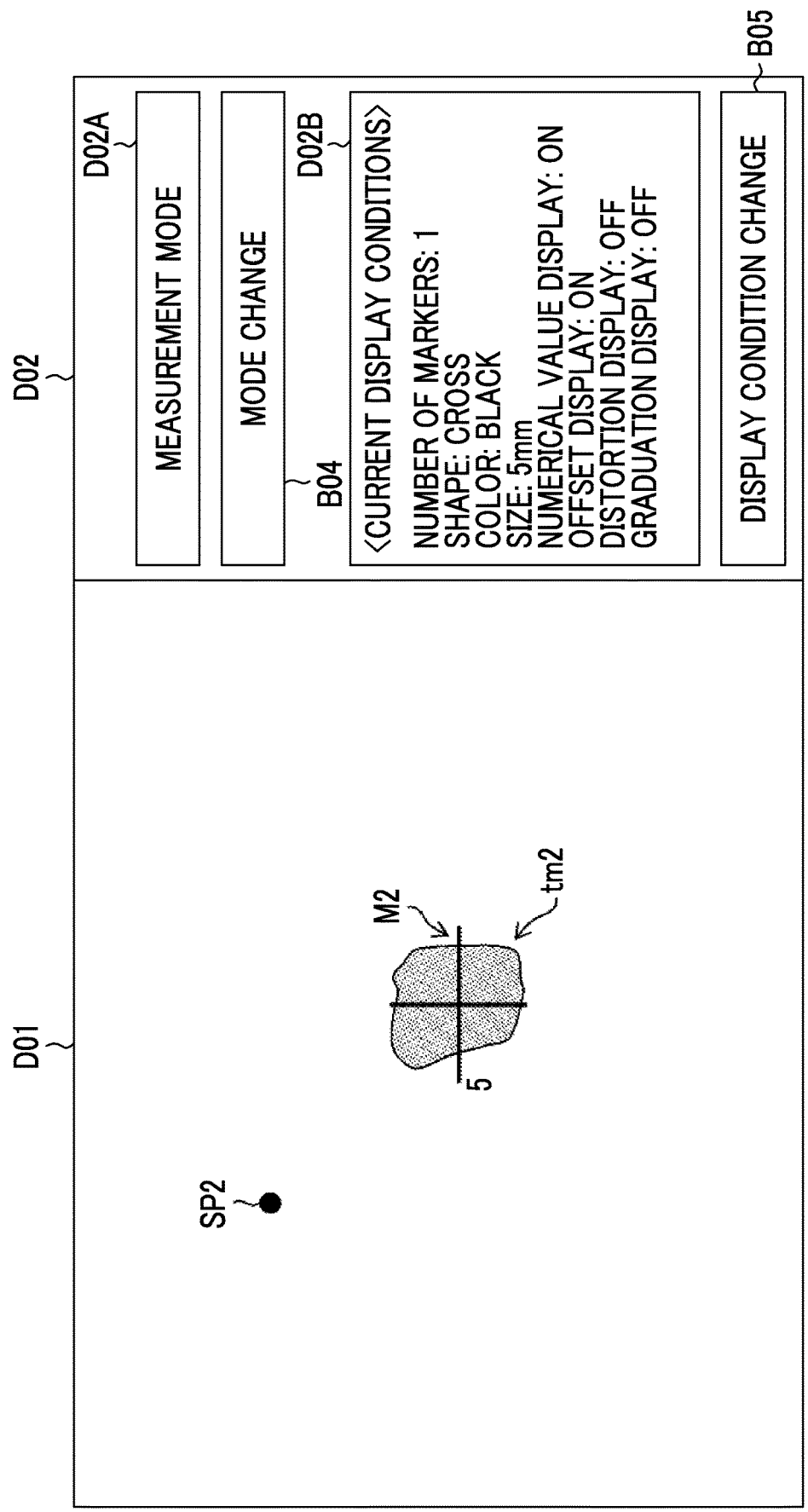
FIG. 23 is a view illustrating a state where the center of a marker is displayed apart from the center of a spot.

In the example of FIG. 21, the marker M1 is displayed with the position of the spot SP1 as a center. This is because the position of the spot SP1 most appropriately indicates the size of the marker. However, the display of the marker is not limited to such an aspect. For example, as illustrated in FIG. 23, by changing the conditions of Example 1 to "Offset Display: ON" via designation of Button B05, the center of a marker M2 may be offset from the center of a spot SP2, and the marker M2 may be displayed on the center of the screen (on a tumor tm2 in FIG. 23). The offset position may be designated by the user. Even in a case where the marker is offset-displayed in this way, there is little influence on measurement accuracy depending on a display position in a case where an observation target directly faces (is not inclined with respect to) the imaging optical system 130.

Example 3

Figure 24:
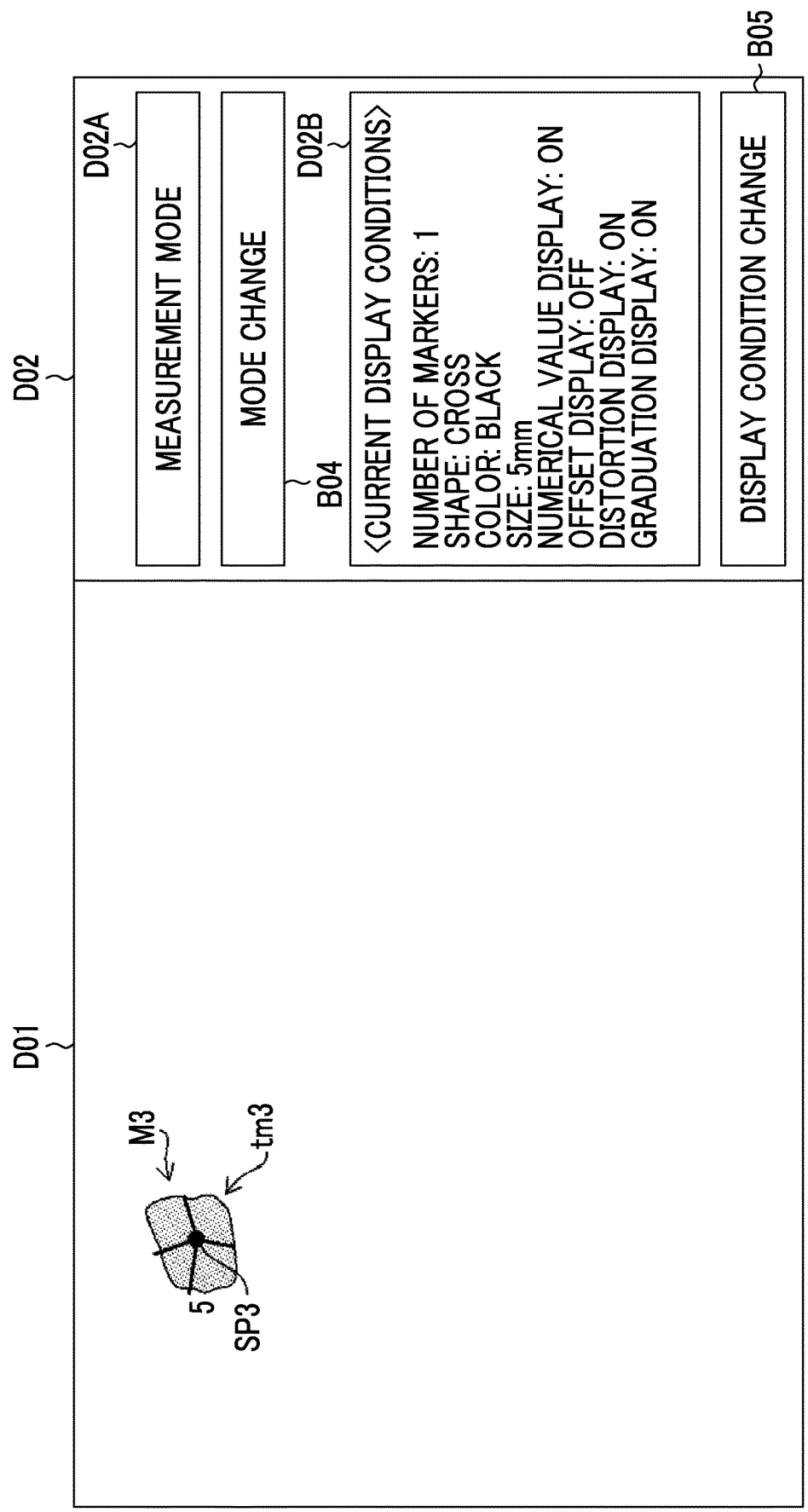
FIG. 24 is a view illustrating a state where a marker is distorted and displayed in accordance with the distortion aberration of the imaging optical system.

Since the distortion aberration of the imaging optical system 130 becomes larger around the imaging field angle, it is preferable to correct the distortion aberration in a case where a marker is displayed on a peripheral portion of a screen. FIG. 24 is a view illustrating a state where a marker is displayed by correcting the influence on the distortion aberration of the imaging optical system 130. With a spot SP3 formed on a tumor tm3 as the center, a marker M3 after distortion aberration correction is displayed. By performing "Distortion Display: ON" via the designation of Button B05, such a display can be performed. In addition, during the correction, data of the distortion aberration may be set on the basis of the design values of the imaging optical system 130 or may be separately measured and acquired. In addition, instead of distorting and displaying a marker, an image of a subject may be corrected in accordance with the distortion aberration, and a marker that is not distorted may be displayed on the image after the correction. Accordingly, the shape or the like of a subject can be accurately displayed and can be measured with high accuracy.

Example 4

Figure 25:
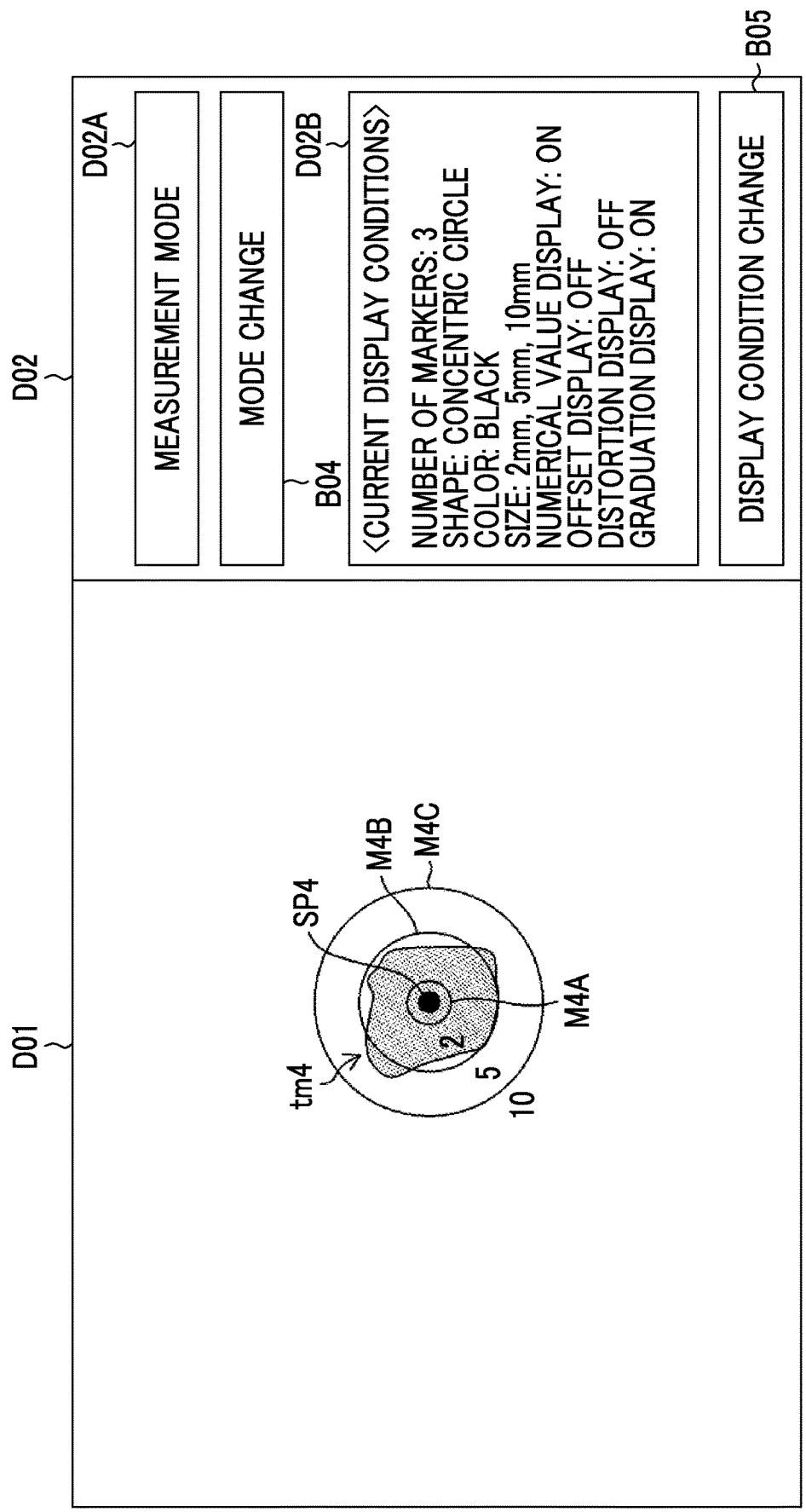
FIG. 25 is a view illustrating a state where concentric markers having three different sizes are displayed.

FIG. 25 is a view illustrating a state where concentric markers M4A, M4B, and M4C (the sizes are respectively 2 mm, 5 mm, and 10 mm in diameter) having three different sizes are displayed with a spot SP4 formed on a tumor tm4 as a center. Since the plurality of markers are displayed, it is possible to save time and labor for switching. Additionally, measurement is easy even in a case where a subject has an asymmetrical shape.

Figure 28:
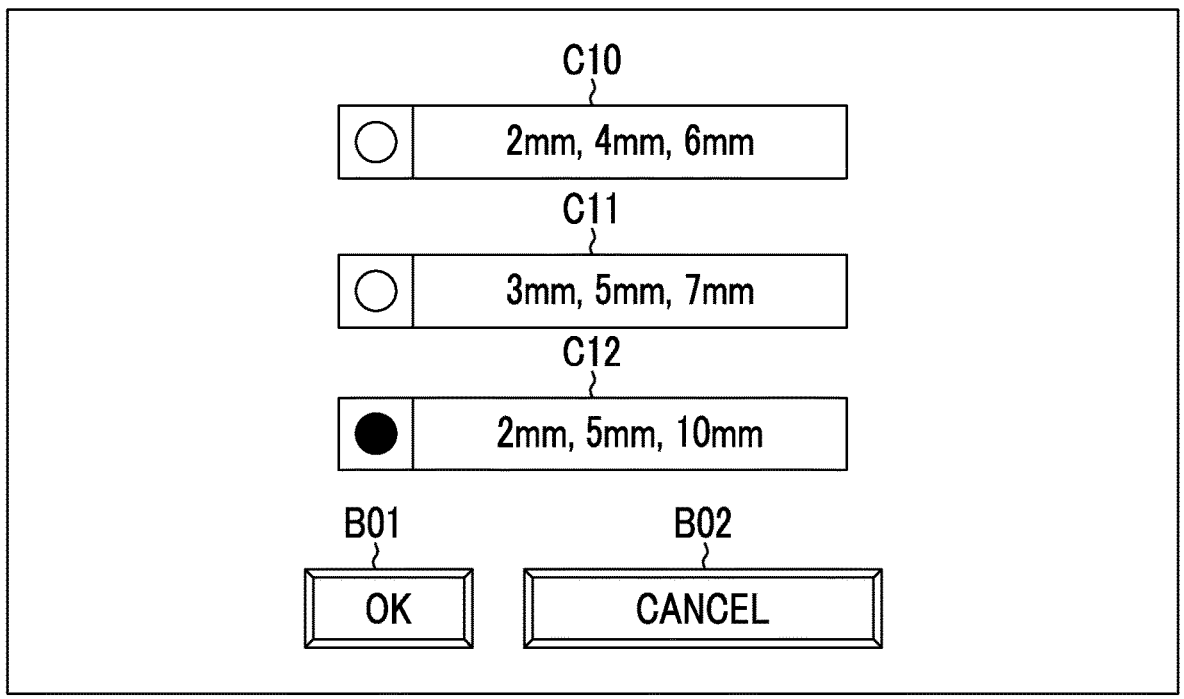
FIG. 28 is a view illustrating a state where combinations of the sizes of markers are selected.

In addition, as illustrated in FIG. 25, in a case where the plurality of markers are displayed, instead of designating size or color for each marker, combinations of a plurality of conditions may be prepared in advance, so that a combination can be selected from the combinations. FIG. 28 illustrates a state where a combination C12 is selected from combinations C10 to C12 of sizes as an example of such a case. In addition, the invention is not limited to such individual conditions (size in the example of FIG. 28), a plurality of combinations like "Number of Markers: 3; Shape: Concentric Circle; Size: 2 mm, 5 mm, 10 mm, Color: Red, White, Blue; Numeral Display: ON; Offset Display: OFF; Distortion Display: OFF and Graduation Display: OFF" may be set for a plurality of items among the display conditions (refer to FIG. 16), and a combination may be selected from the combinations.

In a case where a combination is selected in this way, modes, such as "simultaneously displaying markers of a total of three different sizes including a selected size and sizes before and after the selected size and switching a center size by a user's operation". For example, switching can be made like "(2, 3, 4)-(3, 4, 5)-(4, 5, 7) . . . (20, 30, 50)-(2, 3, 4) . . . (repeated in the following; unit is mm)". In addition, an underlined size is the center size.

By selecting a combination of the display conditions in this way, even in a case where there are many markers, the condition setting can be quickly and easily performed.

Modification Example 1 of Example 4

Figure 26:
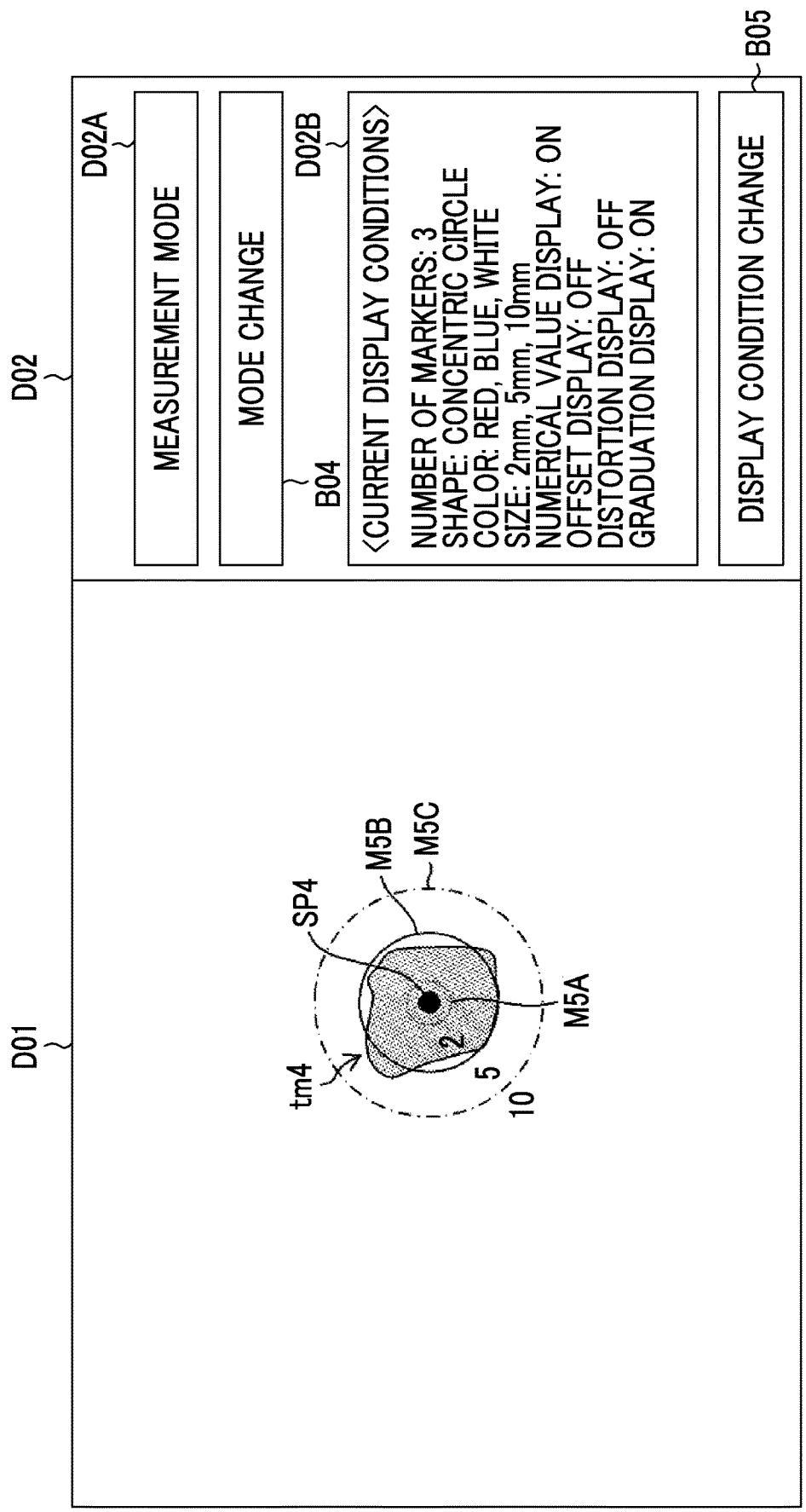
FIG. 26 is a view illustrating a state where concentric markers having three different sizes are respectively displayed in different colors.

In the example illustrated in FIG. 25, all the three markers are displayed in the same color (black). However, in a case where a plurality of markers are displayed, the colors of the markers may be changed. FIG. 26 is a display example in a case where colors of respective markers are changed, and a marker M5A is displayed in red, a marker M5B is displayed in blue, and a marker M5C is displayed in white. In addition, since it is difficult to illustrate differences between the colors, the differences between the colors are illustrated with differences in line type (red is illustrated by a dotted line, blue is illustrated by a solid line, and white is illustrated by one-dot chain line). In this way, by changing the colors of the markers, identification can be improved, and measurement can be easily performed.

Modification Example 2 of Example 4

Figure 27:
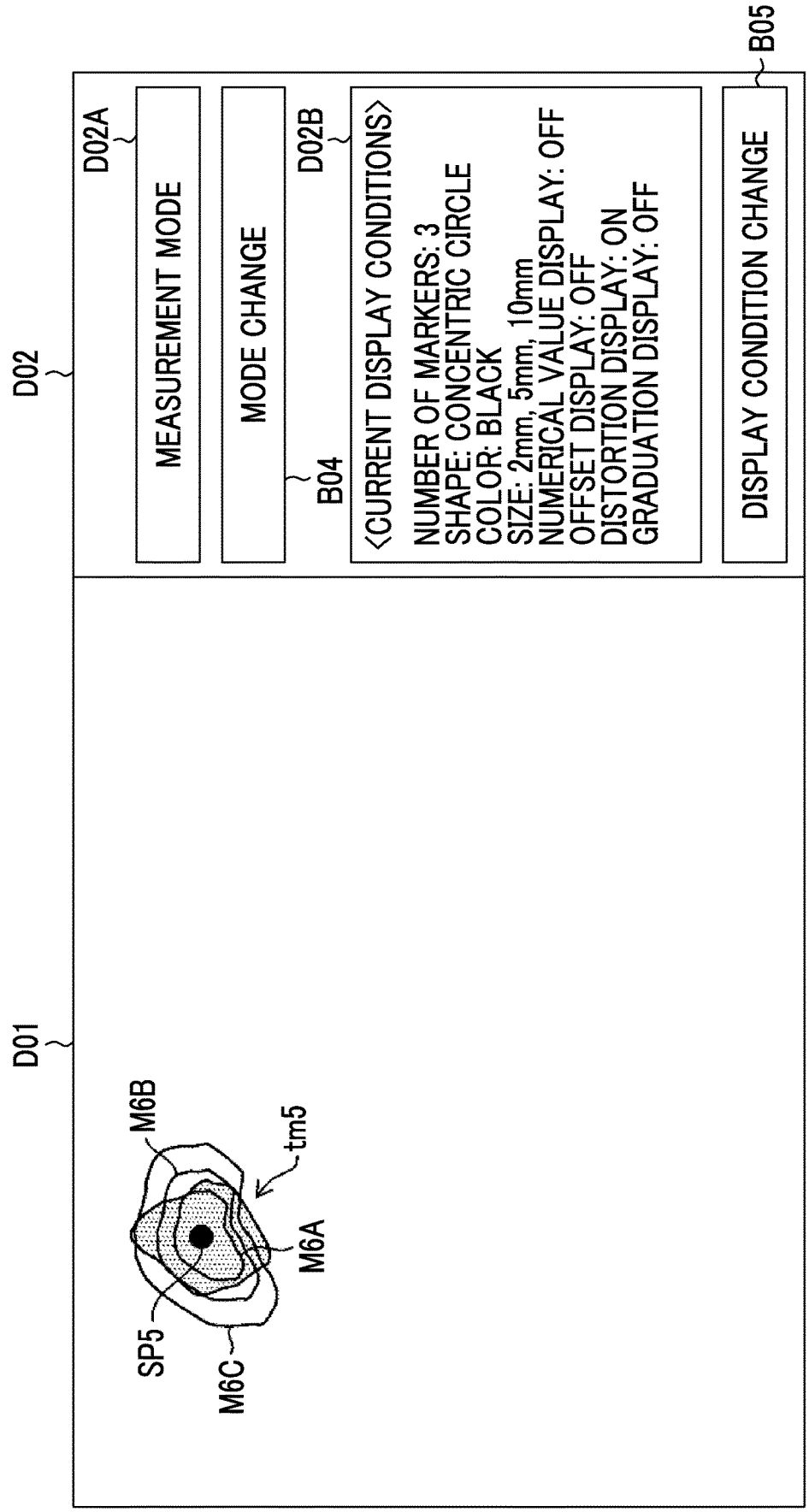
FIG. 27 is a view illustrating a state where concentric markers are distorted and displayed in accordance with the distortion aberration of the imaging optical system.

In a case where the concentric markers are displayed as illustrated in FIGS. 25 and 26, a display example in which the respective markers are set to "Distortion Display: ON" as illustrated in FIG. 24 is illustrated in FIG. 27. In the case of FIG. 27, markers M6A, M6B, and M6C in distorted form rather than perfect concentric circles are displayed with a spot SP5 formed on a tumor tm5 as a center.

<Another Example of Display Condition Setting Operation>

Figure 29:
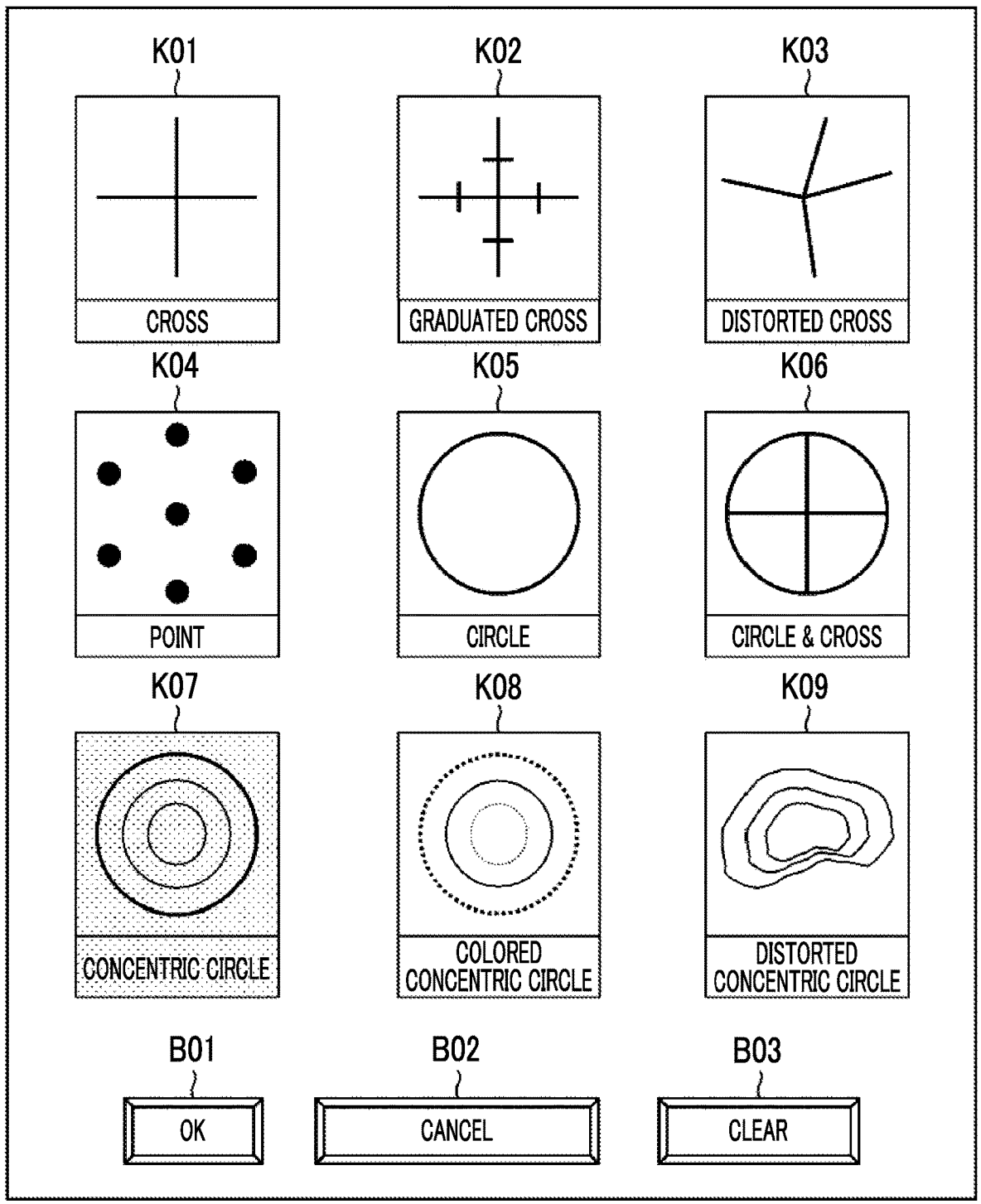
FIG. 29 is a view illustrating a state where display conditions are set by selecting small images illustrating the types of markers.

Next, another example of display condition setting operation will be described. In the example described with reference to FIG. 16, the display conditions of a marker are displayed in characters. However, icon-like small images indicating the type of a marker may be displayed on the display condition setting screen, so that the display conditions can be set by selecting the small images. FIG. 29 is a view illustrating a state of the display condition setting by such small images, small images K01 to K09 indicating different types of markers are displayed, and a small image K07 indicating concentric marker is selected. In a case where other display conditions (size, color, numeral display, and the like) are set from this state, the other display conditions may be set by further selecting small images corresponding to the other display conditions similarly to FIG. 29, or may set by the same operations as those in FIGS. 16 to 20, and the like.

<Measurement of Relationship Between Spot Position and Size of Marker>

In the first embodiment, the relationship between the positions of the spots on the imaging element and the sizes (the numbers of pixels) of the markers corresponding to the actual sizes of the subjects are measured in advance, and is stored in the memory 212 in association with the spot positions, and the size of a marker is calculated with reference to this relationship in accordance with a measured spot position. Hereinafter, an example of a measurement procedure of the relationship between spot positions and the sizes of markers will be described. In addition, here, the markers are cross-shaped and an actual size in the horizontal direction and in the vertical direction is set to 5 mm.

The relationship between the spot positions and the sizes of the markers can be obtained by imaging a chart on which patterns of the actual size are regularly formed. For example, a spot is formed by emitting the measurement auxiliary light, a grid-sheet-like chart of the same ruled lines (5 mm ruled lines) as the actual size or ruled lines (for example, 1 mm ruled lines) finer than the actual size is imaged while changing the observation distance to change the position of the spot, and a relationship between a spot position (pixel coordinates on the imaging surface of the imaging element) and the number of pixels corresponding to the actual size (how many pixels the actual size of 5 mm is represented) is acquired.

Figure 31:
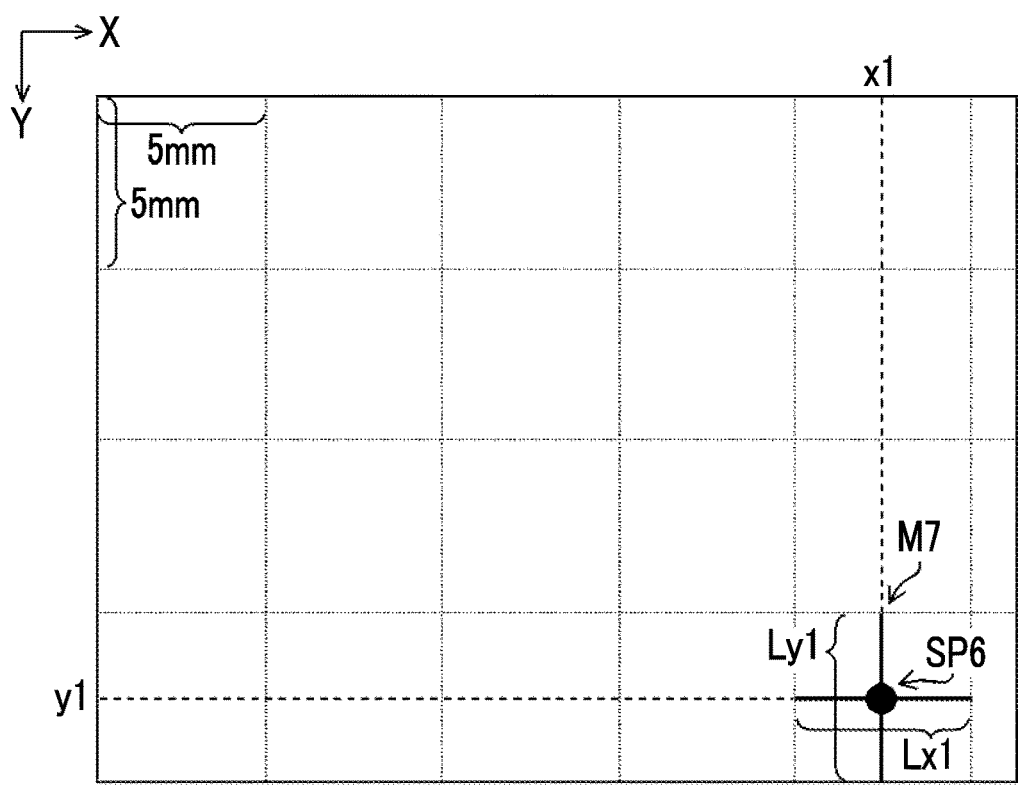
FIG. 31 is a view illustrating a state where a relationship between a spot position and the size of a marker is measured.
Figure 32:
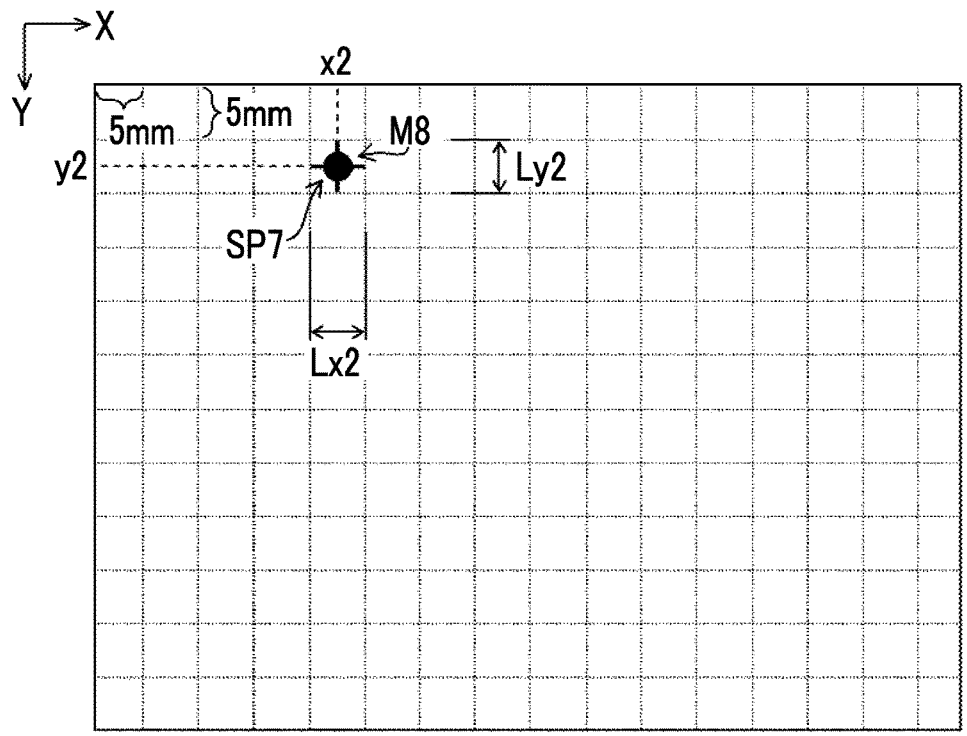
FIG. 32 is a view illustrating another state where a relationship between a spot position and the size of a marker is measured.

FIG. 31 is a view illustrating a state where the chart of the 5 mm ruled lines is imaged. The imaging distance is in a state close to the near end, and the intervals of the ruled lines are wide. In FIG. 31, (x1, y1) indicates an X-, Y-direction pixel position of a spot SP6 on the imaging surface of the imaging element 134. The number of X-direction pixels, corresponding to the actual size of 5 mm, of a marker M7 at the position (x1, y1) of the spot SP6 is set to Lx1, and the number of Y-direction pixels is set to Ly1. Such measurement is repeated while changing the observation distance. Although FIG. 32 is a view illustrating a state where a chart of the same 5 mm ruled lines as those in FIG. 31 is imaged, the imaging distance is in a state closer to the far end than the state of FIG. 31, and the intervals f the ruled lines are narrow. In the state of FIG. 32, the number of X-direction pixels, corresponding to the actual size of 5 mm, of a marker M8 at a position (x2, y2) of a spot SP7 on the imaging surface of the imaging element 134 is set to Lx2, and the number of Y-direction pixels is set to Ly2. The measurement as illustrated in FIGS. 31 and 32 is repeated while changing the observation distance, and results are plotted. In addition, for the convenience description, in FIGS. 31 and 32, display is performed regardless of the distortion aberration of the imaging optical system 130.

Figure 33:
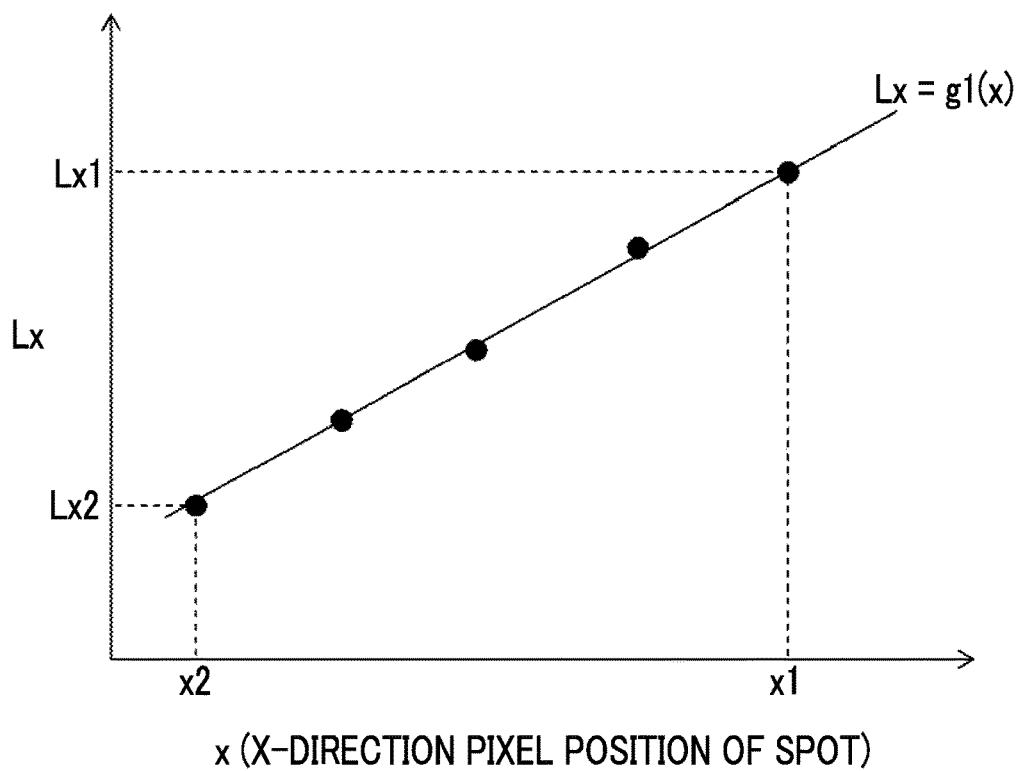
FIG. 33 is a view illustrating a relationship between the X-direction pixel positions of spots and the numbers of pixels of markers in the X-axis direction.
Figure 34:
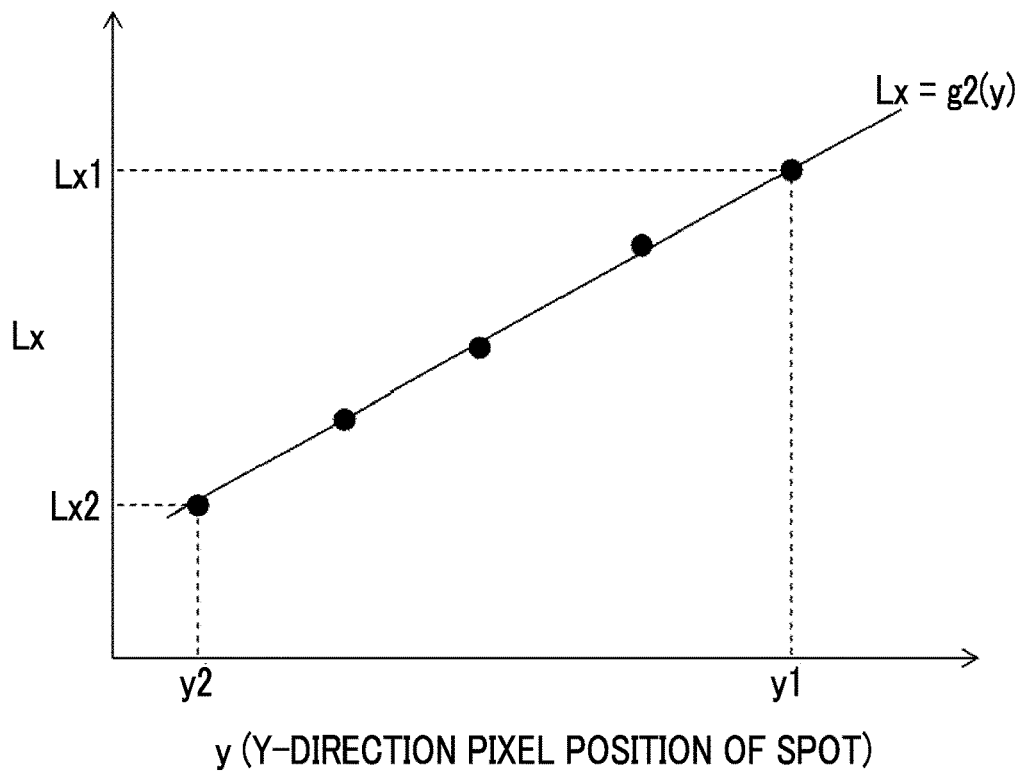
FIG. 34 is a view illustrating a relationship between the Y-direction pixel positions of spots and the numbers of pixels of markers in the X-axis direction.

FIG. 33 is a view illustrating a relationship between X coordinates of spot positions and Lx (the numbers of X-direction pixels of markers), and FIG. 34 is a view illustrating a relationship between Y coordinates of spot positions, and Lx. L(x) is expressed as $Lx=g1(x)$ as a function of X-direction positions from the relationship of FIG. 33, and is expressed as $Lx=g2(y)$ as a function of Y-direction positions from the relationship of FIG. 34. g1 and g2 can be found by, for example, the least-square method from the above-described plot results. In this way, the two functions g1 and g2 indicating Lx are obtained. However, the X coordinates and the Y coordinates of the spots have a one to one correspondence, and basically the same results (the same numbers of pixels for the same spot positions) are obtained even in a case where either g1 or g2 is used. Therefore, any function may be used in a case where the sizes of the markers are calculated. A function with a higher sensitivity of pixel number changes with respect to position changes may be chosen out of g1 and g2. Additionally, in a case where the values of g1 and g2 are greatly different, it may be determined that "A spot could not be recognized."

In the first embodiment, information indicating the functions g1 and g2 obtained in this way is stored in the memory 212 before measurement depending on function forms, look-up table forms, and the like.

Figure 35:
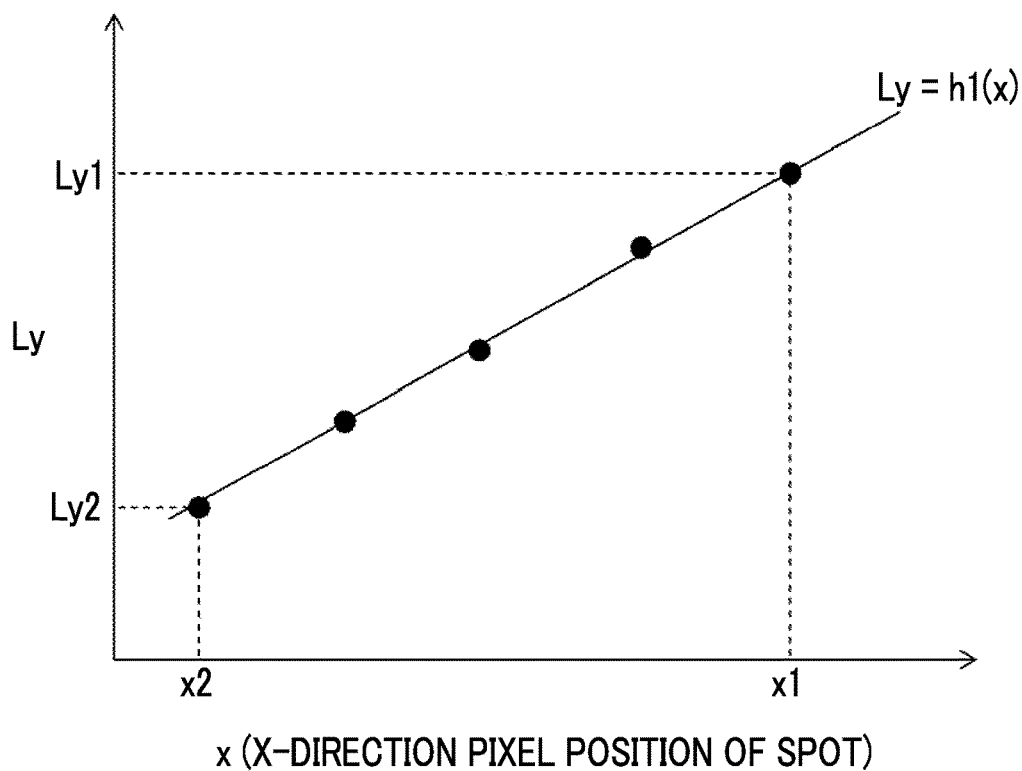
FIG. 35 is a view illustrating a relationship between the X-direction pixel positions of the spots and the numbers of pixels of the markers in the Y-axis direction.
Figure 36:
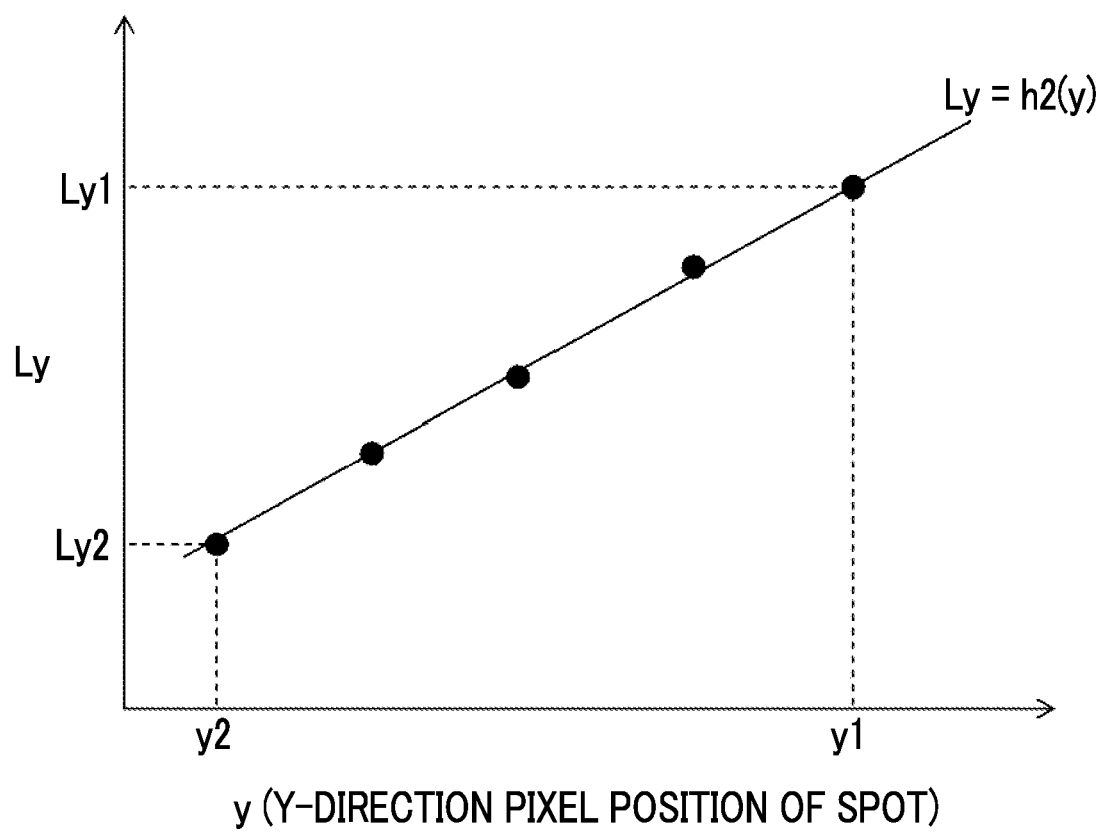
FIG. 36 is a view illustrating a relationship between the Y-direction pixel positions of the spots and the numbers of pixels of the markers in the Y-axis direction.

Additionally, FIG. 35 is a view illustrating a relationship between X coordinates of spot positions and Ly (the numbers of Y-direction pixels), and FIG. 36 is a view illustrating a relationship between Y coordinates of the spot positions, and Ly. L(y) is expressed as Ly=h1(x) as a function of the X-direction positions from the relationship of FIG. 35, and is expressed as Ly=h2(y) as a function of the Y-direction positions from the relationship of FIG. 36. Regarding Ly, similarly to Lx, any of the function h1 and h2 may be used.

<Modification Example of Illumination Light Source>

In the above-described embodiments and modification examples, a case where the light source device 300 (illumination light source) for illumination and observation includes the visible light source 310A (illumination light source), and the infrared light source 310B (illumination light source) has been described. However, in the implementation of the invention, the configuration of the light source is not limited to such an aspect. For example, the light source may be constituted of one or a plurality of LEDs with different wavelengths, such as white; blue, green, and red; or purple, blue, green, and red. In this case, LEDs of respective colors may be made to emit light independently in accordance with observation targets or observation conditions, and LEDs of a plurality of colors may be made to emit light simultaneously. Additionally, white light may be radiated by making LEDs of all monochromatic light emit light simultaneously.

Additionally, the light source device may be constituted of a laser light source for the white light (broadband light) and a laser light source for narrowband light. In this case, the narrowband light can be selected from one wavelength or a plurality of wavelengths, such as blue or purple.

Additionally, the light source may be a xenon light source, and the light source device may be constituted of a light source for normal light (white light) and a light source for narrowband light. In this case, the narrowband light can be selected from one wavelength or a plurality of wavelengths, such as blue or green. For example, wavelengths of the narrowband light to be radiated may be switched by rotating a disk-shaped filter (rotary color filter) disposed in front of the light source and provided with blue and green color filters. In addition, two or more wavelengths of infrared light with different wavelengths may be used instead of blue and green narrowband lights.

It is preferable that the light source type of the light source device, the wavelengths, and the presence or absence of the filters are configured in accordance with the type of subject, the purposes of observation, or the like. Additionally, it is preferable to combine and/or switch the wavelengths of the illumination light in accordance with the type of subject, the purposes of observation, or the like during observation. For example, it is preferable to appropriately combine and or switch the wavelengths of the illumination light between the above-described LED lights of respective colors, between white laser light and first and second narrowband laser lights (blue and purple), between blue narrowband light and green narrowband light or between first infrared light and second infrared light.

<Modification Example of Imaging Element and Imaging Method>

In the above-described embodiments and modification examples, a case where the imaging element 134 is a color imaging element in which color filters are disposed at pixels, respectively, has been described. However, in the invention, the configuration of the imaging element and the imaging method are not limited to such an aspect, and a monochrome imaging element (a CCD type, a CMOS type, or the like) may be used.

In a case where the monochrome imaging element is used, images can be face-sequentially (color-sequentially) captured by sequentially switching the wavelengths of the illumination light. For example, the wavelengths of the illumination light to be emitted may be sequentially switched between purple, blue, green, and red, and the wavelengths of the illumination light to be emitted by rotary color filters (red, green, blue, and the like) may be switched by radiating the broadband light (white light). Additionally, the wavelengths of the illumination light to be emitted by rotary color filters (green, blue, and the like) may be switched by radiating one or a plurality of narrowband lights (green, blue, and the like). The narrowband light may be infrared light of two or more wavelengths having different wavelengths.

<Others>

The endoscope system of the invention, can also be applied to cases where test objects, which are not living bodies, such as a pipe, are measured in addition to measuring the test object that is a living body. Additionally, the endoscope system of the invention can also be applied to cases where the dimensions and shapes of industrial parts and products are measured.

Although the example of the invention has been described above, it is obvious that the invention is not limited to the above-described embodiments and examples, and various modifications can be made without departing from the spirit of the invention.

EXPLANATION OF REFERENCES

10: endoscope system
100: endoscope device
102: proximal Operating part
104: insertion part
106: universal cable
108: light guide connector
110: endoscope body
112: flexible part
114: bending part
116: distal end rigid part
116A: distal-end-side end surface
123: illumination Unit
123A: illuminating lens
123B: illuminating lens
126: forceps port
130: imaging optical system
132: imaging Lens
134: imaging element
136: drive circuit
138: AFE
170: light guide
200: endoscope processor
202: image input controller
204: image processing unit
206: video output unit
208: operating part
210: CPU
212: memory 300: light source device
310: light source
310A: visible light source
310B: infrared light source
330: stop
340: condensing lens
350: light source control unit
400: monitor
500: laser module
501: fiber outer jacket
502: laser light source module
503: condensing Lens
504: optical fiber
506: laser head
507: reinforcing member
508: ferrule
509: housing
510: GRIN Lens
512: prism
A01: button
A01a button
A01c: slide bar
A02: button
A02a button
A02c slide bar
A03: button
A03a: button
A03c: slide bar
A04: button
A04a: button
A04c: slide bar
A05: button
A06: button
A07: button
A08: button
AL1: apex angle
B01 to B05: button
C01 to C08: region
C10 to C12: combination
D01: image display region
D02: information display region
D02A: region
D02B: region
IA: imaging range
K01 to K09: small image
L1: optical axis
L1A: optical axis
L1B: optical axis
L2: optical axis
M1: marker
M2: marker
M3: marker
M4A: marker
M4B: marker
M4C: marker
M5A: marker
M5B: marker
M5C: marker
M6A: marker
M6B: marker
M6C: marker
M7: marker
M8: marker
MS1: warning message
P1: near end
P3: far end
P4 to P9: spot
R1: range
R2: imaging range
R3: imaging range
S10 to S30: respective steps of measuring processing
SP0 to SP7: spot
V01 to V08: region
g1: function
g2: function
h1: function
h2: function
tm: tumor
tm1 to tm5: tumor

What is claimed is:

1. An endoscope system comprising:
an endoscope configured to acquire an image of a subject;
an auxiliary light source configured to radiate measurement auxiliary light to the subject;
an imaging sensor configured to acquire the image of the subject, on which a single spot configured to form with the measurement auxiliary light;
an imaging lens that is disposed on a distal end rigid part of the endoscope and on a same optical path as the imaging sensor;
a measurement auxiliary light head that is disposed on the distal end rigid part of the endoscope and on a same optical path as the auxiliary light source;
a display configured to display the acquired image of the subject;
a processor configured to cause the display to display, together with the image of the subject, an index figure indicating an actual size of a specific region in the subject and having a size set in accordance with a position of the single spot on the imaging sensor as the imaging sensor acquires the image of the subject; and
a plurality of illuminating lenses that are disposed on two sides of an optical axis of the measurement auxiliary light head when viewed from an axial direction of the distal end rigid part, and are disposed on two sides of a line connecting a forceps port and the imaging lens when viewed from the axial direction of the distal end rigid part.

2. The endoscope system according to claim 1, wherein the processor is configured to cause the display to display the index figure distorted in accordance with a distortion aberration of an imaging optical system.

3. The endoscope system according to claim 1, wherein the processor is configured to cause the display to display the index figure together with the image of the subject corrected in accordance with a distortion aberration of an imaging optical system.

4. The endoscope system according to claim 1, wherein the processor is configured to cause the display to display the image of the subject and the index figure in a state where a center of the index figure coincides with a center of the single spot.

5. The endoscope system according to claim 1, wherein the processor is configured to cause the display to display the image of the subject and the index figure in a state where a center of the index figure is separated from a center of the single spot.

6. The endoscope system according to claim 1, wherein the processor is configured to cause the display to display the index figure of a size corresponding to a single value of the actual size.

7. The endoscope system according to claim 1, wherein the processor is configured to cause the display to display the index figure of a size corresponding to a value selected from a plurality of values of actual sizes.

8. The endoscope system according to claim 7, further comprising:
a selection unit configured to receive a user's selection operation for the plurality of values,
wherein the selection unit comprises a touch panel,
wherein the processor is configured to cause the display to display one or a plurality of the index figures of the size corresponding to the value selected on the basis of the selection operation from the plurality of values.

9. The endoscope system according to claim 1, wherein the processor is configured to cause the display to display the index figure of a size corresponding to a combination of a plurality of values of actual sizes.

10. The endoscope system according to claim 9, further comprising:
a selection unit configured to receive a user's selection operation for the combination of the plurality of values,
wherein the selection unit comprises a touch panel,
wherein the processor is configured to cause the display to display the index figure of a size corresponding to a combination selected on the basis of the selection operation.

11. The endoscope system according to claim 1, wherein the processor is configured to cause the display to display another index figure, having a color different than that of the index figure, in correspondence with a value of the actual size.

12. The endoscope system according to claim 1,
wherein the measurement auxiliary light radiated from the auxiliary light source is inclined with respect to an optical axis of the imaging lens, and
wherein, in a case where a distance between the imaging sensor, as well as the auxiliary light source, and the subject is changed in a direction of the optical axis of the imaging lens, a position of the single spot on the imaging sensor in a case where the distance is a longest range of a length measurement distance range of the endoscope is opposite to a position of the single spot on the imaging sensor in a case where the distance is a closest range of the length measurement distance range, with a position of the optical axis of the imaging lens in the imaging sensor interposed therebetween.

13. The endoscope system according to claim 1,
wherein the auxiliary light source is disposed at a proximal portion of the endoscope.

* * * * *